United States Patent
Rigatti et al.

(10) Patent No.: US 11,299,765 B2
(45) Date of Patent: *Apr. 12, 2022

(54) METHODS AND COMPOSITIONS FOR PREPARING SEQUENCING LIBRARIES

(71) Applicant: Illumina Cambridge Limited, Cambridge (GB)

(72) Inventors: Roberto Rigatti, Cambridge (GB); Niall Anthony Gormley, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 76 days.

This patent is subject to a terminal disclaimer.

(21) Appl. No.: 16/561,483

(22) Filed: Sep. 5, 2019

(65) Prior Publication Data
US 2020/0002747 A1    Jan. 2, 2020

Related U.S. Application Data

(63) Continuation of application No. 15/318,258, filed as application No. PCT/GB2015/051735 on Jun. 12, 2015, now Pat. No. 10,443,087.

(60) Provisional application No. 62/012,188, filed on Jun. 13, 2014.

(51) Int. Cl.
| | | |
|---|---|---|
| C40B 30/04 | (2006.01) |
| C12Q 1/6806 | (2018.01) |
| C12Q 1/6874 | (2018.01) |
| C40B 50/06 | (2006.01) |

(52) U.S. Cl.
CPC ......... *C12Q 1/6806* (2013.01); *C12Q 1/6874* (2013.01); *C40B 30/04* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 5,130,238 | A | 7/1992 | Malek et al. |
| 5,185,243 | A | 2/1993 | Ullman et al. |
| 5,223,414 | A | 6/1993 | Darling et al. |
| 5,455,166 | A | 10/1995 | Walker |
| 5,573,907 | A | 11/1996 | Carrino et al. |
| 5,599,675 | A | 2/1997 | Brenner |
| 5,641,658 | A | 6/1997 | Adams et al. |
| 5,679,524 | A | 10/1997 | Nikiforov et al. |
| 5,750,341 | A | 5/1998 | Macevicz |

(Continued)

FOREIGN PATENT DOCUMENTS

| | | | |
|---|---|---|---|
| EP | 0320308 | A2 | 6/1989 |
| EP | 0336731 | A2 | 10/1989 |

(Continued)

OTHER PUBLICATIONS

Extended European Search Report, EP Application No. 20150370.3, dated Aug. 19, 2020, 14 pages.

(Continued)

*Primary Examiner* — Christian C Boesen
(74) *Attorney, Agent, or Firm* — McNeill Baur PLLC

(57) ABSTRACT

Embodiments provided herein relate to methods and compositions for next generation sequencing. Some embodiments include the preparation of a template library from a target nucleic acid in contact with a surface, and sequencing the library on the surface.

15 Claims, 6 Drawing Sheets

(56) References Cited

U.S. PATENT DOCUMENTS

| | | | |
|---|---|---|---|
| 5,925,545 | A | 7/1999 | Reznikoff et al. |
| 5,965,443 | A | 10/1999 | Reznikoff et al. |
| 6,210,891 | B1 | 4/2001 | Nyren et al. |
| 6,258,568 | B1 | 7/2001 | Nyren |
| 6,274,320 | B1 | 8/2001 | Rothberg et al. |
| 7,011,792 | B2 | 3/2006 | Mimura et al. |
| 7,057,026 | B2 | 6/2006 | Barnes et al. |
| 7,083,980 | B2 | 8/2006 | Reznikoff et al. |
| 7,115,400 | B1 | 10/2006 | Adessi et al. |
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,399,590 | B2 | 7/2008 | Piepenburg et al. |
| 7,405,281 | B2 | 7/2008 | Xu et al. |
| 7,582,420 | B2 | 9/2009 | Oliphant et al. |
| 7,595,883 | B1 | 9/2009 | El Gamal et al. |
| 7,608,434 | B2 | 10/2009 | Reznikoff et al. |
| 7,611,869 | B2 | 11/2009 | Fan |
| 7,670,810 | B2 | 3/2010 | Gunderson et al. |
| 8,003,354 | B2 | 8/2011 | Shen et al. |
| 8,563,477 | B2 | 10/2013 | Smith et al. |
| 2001/0044107 | A1 | 11/2001 | Zarling et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2005/0191698 | A1 | 9/2005 | Chee et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2010/0022403 | A1 | 1/2010 | Kum et al. |
| 2010/0111768 | A1 | 5/2010 | Banerjee et al. |
| 2010/0120098 | A1 | 5/2010 | Grunenwald et al. |
| 2010/0137143 | A1 | 6/2010 | Rothberg et al. |
| 2010/0282617 | A1 | 11/2010 | Rothberg et al. |
| 2011/0014657 | A1 | 6/2011 | Rigatti et al. |
| 2012/0028617 | A1 | 2/2012 | Madhavan et al. |
| 2012/0208705 | A1 | 8/2012 | Steemers et al. |
| 2012/0208724 | A1 | 8/2012 | Steemers et al. |
| 2012/0258892 | A1 | 10/2012 | Wang |
| 2012/0270305 | A1 | 10/2012 | Reed et al. |
| 2013/0065783 | A1 | 3/2013 | Prentiss et al. |
| 2013/0196860 | A1 | 8/2013 | Grunenwald et al. |
| 2013/0203605 | A1 | 8/2013 | Shendure et al. |
| 2013/0338042 | A1 | 12/2013 | Shen et al. |
| 2014/0093916 | A1 | 4/2014 | Belyaev |
| 2014/0194324 | A1 | 7/2014 | Gormley et al. |
| 2015/0176071 | A1 | 6/2015 | Fisher et al. |
| 2015/0291942 | A1 | 10/2015 | Gloeckner et al. |

FOREIGN PATENT DOCUMENTS

| | | |
|---|---|---|
| EP | 0439182 A2 | 7/1991 |
| WO | 8909835 | 10/1989 |
| WO | 8910977 | 11/1989 |
| WO | 198912696 A1 | 12/1989 |
| WO | 9001069 | 2/1990 |
| WO | 9106678 A1 | 1/1991 |
| WO | 9523875 | 9/1995 |
| WO | 2004018497 A2 | 3/2004 |
| WO | 2007123744 A2 | 11/2007 |
| WO | 2010048605 A1 | 4/2010 |
| WO | 2012025250 A2 | 3/2012 |
| WO | 2012058096 A1 | 5/2012 |
| WO | 2012061832 A1 | 5/2012 |
| WO | 2013028643 A1 | 2/2013 |
| WO | 2013028643 | 4/2013 |
| WO | 2013131962 A1 | 9/2013 |
| WO | 2014018423 A2 | 1/2014 |
| WO | 2014142850 A2 | 9/2014 |
| WO | 2015095226 A2 | 6/2015 |

OTHER PUBLICATIONS

Third Written Opinion, Singapore Patent Application No. 11201610357U, dated Jun. 26, 2020, 8 pages.
Kim et al., "A microfluidic DNA library preparation platform for next-generation sequencing," PLOS ONE, 2013, 8(7), e68988.
Caruccio, N., "Preparation of next-generation sequencing libraries using Nextera(TM) technology: simultaneous DNA fragmentation and adaptor tagging by in vitro transposition," Methods Mol. Biol. 2011, 733, 241-255.
PCT/GB/2015/051735 International Search Report dated Aug. 13, 2015.
Bains et al., J. Theoretical Biol. 1988, 135(3), 303-307.
Bentley et al., Nature 2008, 456, 53-59.
Boeke et al., Ann. Rev. Microbiol. 1989, 43, 403-34.
Brown et al., Proc. Natl. Acad. Sci. USA 1989, 86, 2525-9.
Cockroft et al., J. Am. Chem. Soc. 2008, 130, 818-820.
Colegio et al., J. Bacteriol. 2001, 183, 2384-8.
Craig, Curr. Topics Microbiol. Immunol. 1996, 204, 27-48.
Draig, Science 1996, 271, 1512.
Deamer and Akeson, Trends Biotechnol. 2000, 18, 147-151.
Deamer and Branton, Acc. Chem. Res. 2002, 35, 817-825.
Dean et al., Proc. Natl. Acad. Sci. USA 2002, 99, 5261-66.
Devine et al., Nucleic Acids Res. 1994, 22, 3765-72.
Drmanac et al., Nature Biotechnology 1998, 16, 54-58.
Fodor et al., Science 1991, 251(4995), 767-773.
Gloor, Methods Mol. Biol. 2004, 260, 97-114.
Goryshin and Reznikoff, J. Biol. Chem. 1998, 273, 7367.
Healy, Nanomed. 2007, 2, 459-481.
Ichikawa et al., J. Biol. Chem. 1990, 265, 18829-32.
Joos et al., Analytical Biochemistry 1997, 247, 96-101.
Khandjian, Mol. Bio. Rep. 1986, 11, 107-11.
Kirby et al., Mol. Microbiol. 2002, 43, 173-86.
Kleckner et al., Curr. Topics Microbiol. Immunol. 1996, 204, 49-82.
Korlach et al., Proc. Natl. Acad. Sci. USA 2008, 105, 1176-1181.
Lage et al., Genome Res. 2003, 13, 294-307.
Lampe et al., EMBO J. 1996, 15, 5470-9.
Levene et al., Science 2003, 299, 682-686.
Li et al., Nat. Mater. 2003, 2, 611-615.
Lizardi et al., Nat. Genet. 1998, 19, 225-232.
Lundquist et al., Opt. Lett. 2008, 33, 1026-1028.
Mizuuchi, Cell 1983, 35, 785.
Ohtsubo et al., Curr. Topics Microbiol. Immunol. 1996, 204, 1-26.
Oroskar et al., Clin. Chem. 1996, 42, 1547-1555.
Plasterk, Curr. Topics Microbiol. Immunol. 1996, 204, 125-42.
Rasila, T.S. et al., PLoS ONE 2012, 7(5), e37922.
Ronaghi et al., Analytical Biochemistry 1996, 242(1), 84-9.
Ronaghi et al., Science 1998, 281(5375), 363.
Ronaghi, Genome Res. 2001, 11(1), 3-11.
Savilahti et al., EMBO J. 1995, 14, 4893-4903.
Shendure et al., Science 2005, 309, 1728-1732.
Smith et al., Science 1992, 253, 1122.
Soni & Meller, Clin. Chem. 2007, 53, 1996-2001.
Taylor et al., 1. Phys. D: Appl. Phys. 1991, 24, 1443.
Walker et al., Molecular Methods for Virus Detection, Academic Press, Inc. 1995.
Walker et al., Nucl. Acids Res. 1992, 20, 1691-96.
Wilson et al., Microbiol. Methods 2007, 71, 332-5.
Ku et al., EMBO Rep., 2004, 5, 795-800.
Zhang et al., PLoS genet. 5:el000689, Epub Oct. 16, 2009.
Ma, Z., et al., "Isothermal amplification method for next-generation sequencing," Proc. Natl. Acad. Sci. 2013, 110(35), 14320-14323.
Syed, F. et al., "Next generation sequencing library preparation, simultaneous fragmentation and tagging using in vitro transposition," Nature Methods 2009, 6, i-ii.
Kersting et al., Microchim Acta, 2014, 181(13),1715-1723.

METHODS AND COMPOSITIONS FOR PREPARING SEQUENCING LIBRARIES

RELATED APPLICATIONS

This application is a continuation of U.S. application Ser. No. 15/318,258, filed Dec. 12, 2016, issued as U.S. Pat. No. 10,443,087, which is the national stage application of International Application No. PCT/GB2015/051735, filed on Jun. 12, 2015, which claims priority to U.S. Provisional Application No. 62/012,188, filed on Jun. 13, 2014, the contents of which are hereby incorporated herein by reference in their entireties.

FIELD OF THE INVENTION

Embodiments provided herein relate to methods and compositions for next generation sequencing. Some embodiments include the preparation of a template library from a target nucleic acid in contact with a surface, and sequencing the library on the surface.

BACKGROUND OF THE INVENTION

Several next generation sequencing technologies are available for fast and economical determination of a genome's entire sequence. Typically, a library of template nucleic acids is prepared from a target genomic DNA sample prior to sequencing. The sample preparation usually includes a DNA fragmentation step that breaks the larger DNA strands into smaller DNA fragments that are more amenable to next generation sequencing technologies. Oftentimes adaptors are attached to the ends of the DNA fragments, which can be accomplished by DNA end repair followed by adaptor ligation, or more recently by using a transposome system. The use of transposomes, which is a complex of a transposase and transposon sequences, allows for simultaneous genomic fragmentation and adaptor ligation of fragments thereby simplifying library preparation. Library preparation methods are typically labor intensive and require several hands-on steps at different stages. Therefore, a need exists for more efficient stream-lined library preparation methods.

SUMMARY OF THE INVENTION

One embodiment of the invention is a method of preparing a population of target nucleic acids for sequencing comprising: (a) providing a substrate having a surface comprising a capture moiety; (b) contacting the surface with a reaction volume comprising a plurality of template nucleic acids and transposomes, wherein each transposome comprising a transposon sequence and the transposase, wherein the template nucleic acids are prepared by contacting a target nucleic acid with a plurality of transposomes; and (c) associating the template nucleic acids with the capture moiety. Some embodiments further comprise, (d) sequencing the associated template nucleic acids. Some embodiments further comprise, amplifying the associated template nucleic acids after (c) and before (d). In some embodiments, the capture moiety of the surface is a capture probe immobilized to the surface. In some embodiments, the capture moiety of the surface is a first affinity moiety and the template nucleic acids comprises a second affinity moiety having affinity for the first affinity moiety. In some embodiments the amplifying comprises bridge amplification. In some embodiments (a) further comprises providing a sample comprising the target nucleic acid and the transposomes. In some embodiments the sample comprises a polymerase or a ligase.

In some embodiments the template nucleic acids are prepared by contacting the target nucleic acid with the plurality of transposomes in the presence of the surface. In some embodiments the template nucleic acids are prepared by contacting the target nucleic acid with the plurality of transposomes before the contacting of the surface with the reaction volume comprising a plurality of template nucleic acids and transposases. In some embodiments a polymerase or a ligase is added to the reaction volume after contacting the surface with the reaction volume. In some embodiments a polymerase or a ligase is added to the reaction volume before contacting the surface with the reaction volume. In some embodiments (c) comprises extending the template nucleic acids with the polymerase or ligase. In some embodiments the capture probes comprise nucleic acids. In some embodiments (c) comprises hybridizing the template nucleic acids with the capture probes. In some embodiments (c) comprises preparing single-stranded template nucleic acids. In some embodiments (c) comprises contacting the capture probes and the template nucleic acids with a recombinase.

In some embodiments the template nucleic acids, the capture probes and/or the surface each comprise an affinity moiety. In some embodiments the affinity moiety is selected from the group consisting of biotin, avidin, and streptavidin. In some embodiments (c) comprises binding the affinity moiety of the template nucleic acids with the affinity moiety of the capture probes. In some embodiments (c) comprises binding the affinity moiety of the template nucleic acids with the affinity moiety of the surface. In some embodiments the transposon sequence comprises a sequence selected from the group consisting of a barcode, a sequencing primer, and a fragmentation site. Some embodiments further comprise cleaving the fragmentation site. In some embodiments the fragmentation site is cleaved after (c). In some embodiments at least one transposome comprises two transposon sequences. In some embodiments the transposon sequences are different. In some embodiments the transposase is removed after (b). In some embodiments the transposase is removed after (c). In some embodiments the transposase is removed by contacting the transposase with a protease. In some embodiments the transposase is removed by contacting the transposase with Sodium Dodecyl Sulfate (SDS). In some embodiments the transposase is selected from the group consisting of Tn5, variant of Tn5, hyperactive Tn5, Tn10, and Mu.

In some embodiments at least one transposome is different from at least one other transposome. In some embodiments the proximity of the template nucleic acids on the surface is used to determine the proximity of sequences obtained from the template nucleic acids in a linear representation of the target nucleic acid sequence. In some embodiments, the template nucleic acids in closer proximity to one another on the surface are determined to comprise sequences in closer proximity in the representation of the target nucleic acid sequence compared to template nucleic acids in less close proximity. In some embodiments the representation of the target nucleic acid sequence comprises haplotype information.

In some embodiments the target nucleic acid is selected from the group consisting of DNA and RNA. In some embodiments the target nucleic acid is selected from the group consisting of genomic DNA and cDNA. In some embodiments the target nucleic acid is genomic DNA.

In some embodiments the substrate is selected from the group consisting of at least one bead, slide, flow cell, channel, dip-stick, and well. In some embodiments the surface comprises at least about 10,000 associated template nucleic acids per mm$^2$. In some embodiments the surface comprises at least about 100,000 associated template nucleic acids per mm$^2$. In some embodiments the surface comprises at least about 1,000,000 associated template nucleic acids per mm$^2$.

One embodiment of the invention is a reaction vessel for sequencing a target nucleic acid comprising: a substrate comprising a surface having a plurality of capture probes attached thereto; and a reaction volume in fluid communication with the surface comprising: a plurality of transposomes, each transposome comprising a transposon sequence and the transposase, a plurality of template nucleic acids prepared by contacting a target nucleic acid with a plurality of transposomes, and a polymerase, dNTPs, and/or ligase. In some embodiments the capture probes are attached at sites that form a repeating pattern on the surface. In some embodiments the capture probes are restricted to the sites on the surface and absent at interstitial regions between the sites. In some embodiments the reaction volume simultaneously comprises reactants for reaction steps comprising: transposing the transposon sequences into the target nucleic acid; extending the template nucleic acids with the polymerase and/or ligase; and associating the template nucleic acids with the capture probes. In some embodiments the reaction steps comprising: transposing the transposon sequences into the target nucleic acid; extending the template nucleic acids with the polymerase for at least few bases, followed by ligation.

In some embodiments the reaction volume is configured for a reaction step comprising removing the transposase in the presence of a protease. In some embodiments the reaction volume is configured for associating the template nucleic acids with the capture probes in the presence of a recombinase. In some embodiments the reaction volume is configured for amplifying the template nucleic acids associated with the capture probes. In some embodiments the amplification is bridge amplification. In some embodiments the reaction volume comprises reagents for sequentially transposing the transposon sequences into the target nucleic acid; then extending the template nucleic acids with the polymerase or ligase; and then associating the template nucleic acids with the capture probes. In some embodiments the reaction volume comprises reagents for sequentially transposing the transposon sequences into the target nucleic acid; then extending the template nucleic acids with the polymerase for at least few bases and a ligase. In some embodiments the reaction volume comprises reagents for removing the transposase in the presence of a protease. In some embodiments the reaction volume comprises SDS for removing the transposase. In some embodiments the reaction volume comprises reagents for associating the template nucleic acids with the capture probes in the presence of a recombinase.

In some embodiments the reaction volume comprises reagents for amplifying template nucleic acids associated with the capture moieties. In some embodiments, the capture moiety of the surface is a capture probe immobilized to the surface. In some embodiments, the capture moiety of the surface is a first affinity moiety and the template nucleic acids comprises a second affinity moiety having affinity for the first affinity moiety. In some embodiments the template nucleic acids are associated with the capture probes. In some embodiments the capture probes comprise nucleic acids. In some embodiments the template nucleic acids are hybridized to the capture probe. In some embodiments at least one of the template nucleic acids and at least one of the capture probes each comprise an affinity moiety. In some embodiments the affinity moiety is selected from the group consisting of biotin, avidin, and streptavidin. In some embodiments the capture probes comprise a recombinase. In some embodiments the affinity moiety of at least one of the template nucleic acids is attached to the affinity moiety of at least one of the capture probe. In some embodiments the affinity moiety of at least one of the template nucleic acids is attached to the affinity moiety of the surface. In some embodiments the transposase is selected from the group consisting of Tn5, variant of Tn5, hyperactive Tn5, Tn10, and Mu. In some embodiments the transposon sequence comprises a sequence selected from the group consisting of a barcode, a sequencing primer, and/or a fragmentation site. In some embodiments the transposome comprises two transposons. In some embodiments the transposon sequences are different from each other.

In some embodiments the target nucleic acid is selected from the group consisting of DNA and RNA. In some embodiments the target nucleic acid is selected from the group consisting of genomic DNA and cDNA. In some embodiments the target nucleic acid is genomic DNA.

In some embodiments the substrate is selected from the group consisting of at least one bead, slide, flow cell, channel, dip-stick, and well. In some embodiments the template nucleic acids are associated with the capture probes. In some embodiments the surface comprises at least about 10,000 template nucleic acids per mm$^2$. In some embodiments the surface comprises at least about 100,000 template nucleic acids per mm$^2$. In some embodiments the surface comprises at least about 1,000,000 template nucleic acids per mm$^2$.

In some embodiments the proximity of sequence information obtained from two template nucleic acids in a linear representation of the target nucleic acid sequence is indicative of the proximity of the template nucleic acids on the surface. In some embodiments template nucleic acids in closer proximity to one another on the surface comprise sequences in closer proximity in a representation of the target nucleic acid sequence compared to template nucleic acids in less close proximity. In some embodiments the representation of the target nucleic acid sequence comprises a haplotype representation.

One embodiment of the invention is a flow cell comprising any of the reaction vessels disclosed herein.

One embodiment of the invention is a system for sequencing a target nucleic acid comprising: any of the reaction vessels disclosed herein; a thermocycler for modulating the temperature of the reaction vessel; and a detector for collecting signals from the reaction vessel. Some embodiments comprise a processor comprising instructions to modulate the temperature of the reaction vessel to perform steps comprising: transposing the transposon sequences into the target nucleic acid, extending the template nucleic acids with the polymerase or ligase, and associating the template nucleic acids with the capture probes. In some embodiments, the template nucleic acids are extended at least one base with a polymerase prior to ligation. In some embodiments the instructions to modulate the temperature of the reaction vessel to perform steps comprises amplifying the template nucleic acids associated with the capture probes. In some embodiments the amplification is bridge amplification.

DETAILED DESCRIPTION

Figure 1:
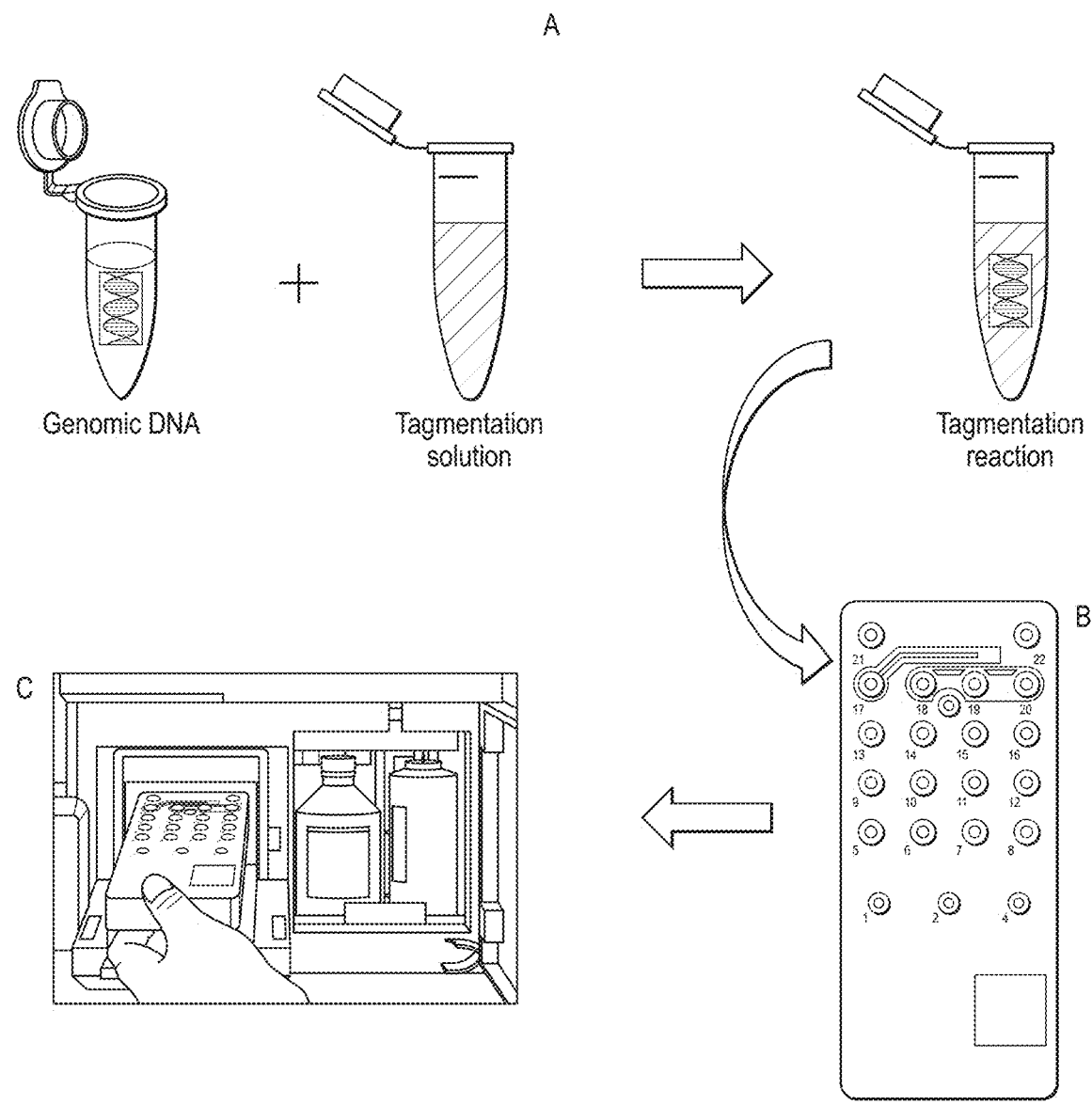
FIG. 1 shows an example embodiment of a simplified workflow for PCR-free automated library preparation in which (A) genomic DNA is mixed with a tagmentation solution that includes trasposomes that can insert into and fragment the genomic DNA, a DNA polymerase and dNTPs; (B) the tagmentation reaction volume is loaded on to a cartridge (e.g. MySeq cartridge); (C) the cartridge is loaded into a system that modulates the temperature of the cartridge, performs a sequencing reaction and obtains sequencing information. The tagmentation reaction comprising the genomic DNA can be loaded inside the cartridge by the system

Embodiments provided herein relate to methods and compositions for next generation sequencing. Some embodiments include the preparation of a template library from a target nucleic acid in contact with a surface, and sequencing the library on the surface.

Typically, methods to prepare a library of sequencing templates for next generation sequencing include multiple steps and transfers of reaction volumes between vessels. In some methods, transposon sequences are inserted into a target nucleic acid, such as genomic DNA. In some methods, the insertion of the transposon sequences can fragment the target nucleic acid into a plurality of modified nucleic acids. The inserted transposon sequences can include sequencing primer sites, amplification primer sites, and/or sites that can anneal to capture probes on a surface, such as a flow cell. In some methods, the modified nucleic acids are amplified with tailed-primers to add sequencing primer sites, amplification primer sites, and/or sites that can anneal to capture probes on a surface. The modified nucleic acids are captured on a surface, amplified by bridge amplification to form clusters on the surface, and sequenced. Typically, the multiple steps including wash steps, and transfers between reaction vessels can be inefficient.

Some embodiments provided herein include methods and compositions for preparing a library of sequencing templates for next generation sequencing in which the library is prepared in a single reaction volume (e.g. a "single pot" reaction or reaction that does not include physical removal of reagents or products prior to completion of the reaction). In some embodiments, a library is prepared in contact with a surface, such as a flow cell, and sequenced on the surface. In some embodiments, a library is prepared in a single reaction volume, and the reaction volume is contacted with a surface and sequenced on the surface (e.g., loaded into a flow cell where library preparation and sequencing reactions occur). Advantageously, some such embodiments increase efficiency in both the yield of sequencing templates obtained from a target nucleic acid, and the time for preparing and sequencing a template library. For example, in some embodiments, there is a reduced need to amplify nucleic acids during the preparation of template library due to the increase in efficiency.

In some embodiments, the physical proximity of template nucleic acids on a surface is related to the proximity of the sequences of those templates in a linear representation of the target nucleic acid from which they are derived. Thus, the preparation of a template library from a target genomic nucleic acid on a surface can advantageously maintain haplotype or phasing information. In other words, contiguity information can be retained. Without wishing to be bound to any one theory, in some embodiments, transposon sequences insert into and fragment a target nucleic acid, the transposase which catalyzes the insertion holds on to each end of the cleavage site, and the modified nucleic acids are immobilized on a surface before the transposase is removed. In some embodiments, bridge amplified clusters within a given distance from one another will have a significant probability of having come from the same segment of original genomic DNA.

In some embodiments, target nucleic acids are captured on a surface, such as a flow cell, fragmented in situ, and allowed to diffuse and seed, forming a cloud of clusters centered around the initial capture site. After sequencing, during assembly, a distance metric (e.g., a normalized physical separation between clusters in a flow cell) can be used to assess whether two reads should be assembled together, considered phased, or used to correct errors in each other (e.g., complementary strands from the same original molecule).

FIG. 1 depicts an embodiment of a workflow useful with some of the methods and compositions provided herein. In this embodiment, (A) an amount of genomic DNA is transferred into a tagmentation solution to yield a tagmentation reaction; (B) the tagmentation reaction is loaded into a MiSeq cartridge (Illumina Inc., San Diego Calif.); and (C) the cartridge is loaded into a MiSeq instrument (Illumina Inc., San Diego Calif.). An automated script performs the tagmentation reaction inside the flow cell. The library molecules generated during the tagmentation are extended by the DNA polymerase present in the tagmentation reaction and are subsequently hybridized to oligonucleotides immobilized on the surface of the flow cell. Each captured molecule is amplified into a cluster by bridge amplification. The nucleic acids of the clusters are linearized, sequencing primers are hybridized to the linear molecules, and the molecules are sequenced. An operator would mix genomic DNA with the tagmentation solution and load the tagmentation reaction onto the sequencer, such as a MiSeq cartridge and MiSeq instrument. Such an example workflow removes upstream sample preparation steps as such steps are performed inside the flow cell.

As used herein, "nucleic acid" includes at least two nucleotide monomers linked together. Examples include, but are not limited to DNA, such as genomic or cDNA; RNA, such as mRNA, sRNA or rRNA; or a hybrid of DNA and RNA. As apparent from the examples below and elsewhere herein, a nucleic acid can have a naturally occurring nucleic acid structure or a non-naturally occurring nucleic acid analog structure. A nucleic acid can contain phosphodiester bonds; however, in some embodiments, nucleic acids may have other types of backbones, comprising, for example, phosphoramide, phosphorothioate, phosphorodithioate, O-methylphosphoroamidite and peptide nucleic acid backbones and linkages. Nucleic acids can have positive backbones; non-ionic backbones, and non-ribose based backbones. Nucleic acids may also contain one or more carbocyclic sugars. The nucleic acids used in methods or compositions herein may be single stranded or, alternatively double stranded, as specified. In some embodiments a nucleic acid can contain portions of both double stranded and single stranded sequence, for example, as demonstrated by forked adapters. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc. In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

As used herein, "nucleotide sequence" includes the order and type of nucleotide monomers in a nucleic acid polymer. A nucleotide sequence is a characteristic of a nucleic acid molecule and can be represented in any of a variety of formats including, for example, a depiction, image, electronic medium, series of symbols, series of numbers, series of letters, series of colors, etc. The information can be represented, for example, at single nucleotide resolution, at higher resolution (e.g. indicating molecular structure for nucleotide subunits) or at lower resolution (e.g. indicating chromosomal regions, such as haplotype blocks). A series of "A," "T," "G," and "C" letters is a well-known sequence representation for DNA that can be correlated, at single nucleotide resolution, with the actual sequence of a DNA molecule. A similar representation is used for RNA except that "T" is replaced with "U" in the series.

As used herein, a "haplotype" includes a set of alleles at more than one locus inherited by an individual from only one of its parents. A haplotype can include two or more loci from all or part of a chromosome. Alleles include, for example, single nucleotide polymorphisms (SNPs), short tandem repeats (STRs), gene sequences, chromosomal insertions, chromosomal deletions etc. The term "phased alleles" refers to the distribution of the particular alleles from a particular chromosome, or portion thereof. Accordingly, the "phase" of two alleles can refer to a characterization or representation of the relative location of two or more alleles on one or more chromosomes.

As used herein, "flow cell" includes a chamber having a surface across which one or more fluid reagents can be flowed. Generally, a flow cell will have an ingress opening and an egress opening to facilitate flow of fluid. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 071123744; U.S. Pat. Nos. 7,329,492; 7,211,414; 7,315,019; 7,405,281, and US Pat. App. Pub. No. 2008/0108082, each of which is incorporated herein by reference in its entirety.

Target Nucleic Acids

Some embodiments of the methods and compositions provided herein include a target nucleic acid. In some embodiments, a target nucleic acid includes genomic DNA, or cDNA. In some embodiments, mitochondrial or chloroplast DNA is used. In some embodiments, target nucleic acids include RNA or derivatives thereof such as mRNA or cDNA. Some embodiments described herein can utilize a single target nucleic acid species, present in one copy (i.e. single molecule) or, alternatively present in multiple copies (i.e. an ensemble of nucleic acid molecules having the same sequence). Other embodiments can utilize a plurality of different target nucleic acid species (e.g., nucleic acid molecules having different nucleotide sequences being present in the plurality). Thus, a plurality of target nucleic acids can include a plurality of target nucleic acids that are all the same as each other, a plurality of different target nucleic acids where some target nucleic acids are the same as each other and some are different from others in the plurality, or a plurality of target nucleic acids where all target nucleic acids are different from all other target nucleic acids in the plurality. Target nucleic acids may be prepared from nucleic acid molecules obtained from a single organism or from populations of nucleic acid molecules obtained from sources that include more than one organism. A target nucleic acid can be from a single cell; from multiple cells, tissue(s) or bodily fluids of a single organism; from cells, tissues or bodily fluids of several organisms of the same species; or from multiple species, as with metagenomic samples, such as from environmental samples. Sources of nucleic acid molecules include, but are not limited to, organelles, cells, tissues, organs, or organisms.

In some embodiments, a target nucleic acid is contacted with a transposome such that a transposon catalyzes insertion of a transposon sequence into the target nucleic acid to provide a modified nucleic acid.

Transposomes

Some embodiments of the methods and compositions provided herein include transposomes. In some embodiments, a transposome includes a transposase bound to one or more transposon sequences. A transposase includes an enzyme that is capable of forming a functional complex with a transposon sequence comprising a transposon element or transposase element, and catalyzing insertion or transposition of the transposon sequence into a target nucleic acid to provide a modified nucleic acid. For example, in an in vitro transposition reaction, inserting transposon sequences into a target DNA to provide a modified DNA. Insertion of the transposon sequences by the transposase can be at a random or substantially random site in the target nucleic acid. Transposases also include integrases from retrotransposons and retroviruses transposases. Exemplary transposases include, but are not limited to Mu, Tn10, Tn5, and hyperactive Tn5 (Goryshin and Reznikoff, J. Biol. Chem., 273: 7367 (1998)). Embodiments of transposases useful with some of the methods and compositions provided herein include those disclosed in U.S. Pat. App. Pub. No. 2010/0120098, which is incorporated herein by reference in its entirety. More embodiments of transposases and transposon elements include a hyperactive Tn5 transposase and a Tn5-type transposase element (Goryshin and Reznikoff, J. Biol. Chem., 273:7367 (1998), which is incorporated herein by reference in its entirety), MuA transposase and a Mu transposase element comprising R1 and R2 end sequences (Mizuuchi, Cell, 35: 785, (1983) and Savilahti, et al., EMBO J., 14: 4893, 15 (1995), each of which is incorporated herein by reference in its entirety). Example transposase elements that form a complex with a hyperactive Tn5 transposase (e.g., EZ-Tn5™ Transposase, Epicentre Biotechnologies, Madison, Wis.) are set forth in WO 2012/061832; U.S. 2012/0208724, U.S. 2012/0208705 and WO 2014018423, each of which is incorporated herein by reference in its entirety. More embodiments of transposases and transposon sequences useful with some of the methods and compositions provided herein include *Staphylococcus aureus* Tn552 (Colegio et al., J. Bacteriol., 183: 2384-8 (2001); Kirby et al., Mol. Microbiol., 43: 173-86 (2002)), Ty1 (Devine & Boeke, Nucleic Acids Res., 22: 3765-72 (1994) and WO 95/23875), Transposon Tn7 (Craig, Science 271: 1512 (1996); Craig, Curr Top Microbiol Immunol., 204:27-48 (1996)), Tn/O and IS10 (Kleckner et al., Curr Top Microbiol Immunol., 204:49-82 (1996)), Mariner transposase (Lampe et al., EMBO J., 15: 5470-9, (1996)), Tel (Plasterk, Curro Topics Microbiol. Immunol., 204: 125-43, (1996)), P Element (Gloor, Methods Mol. Biol., 260: 97-114, (2004)), Tn3 (Ichikawa & Ohtsubo, J Biol. Chem. 265: 18829-32, (1990)), bacterial insertion sequences (Ohtsubo & Sekine, Curro Top. Microbiol. Immunol. 204: 1-26, (1996)), retroviruses (Brown, et al., Proc Natl Acad Sci USA, 86:2525-9, (1989)), and retrotransposon of yeast (Boeke & Corces, Annu Rev Microbiol. 43:403-34, (1989)). More examples include ISS, Tn10, Tn903, IS911, and engineered versions of transposase family enzymes (Zhang et al., PLoS Genet. 5:e1000689. Epub 2009 Oct. 16; and Wilson et al. Microbiol. Methods 71:332-5 (2007)). More examples include MuA transposases (See e.g., Rasila T S, et al., (2012) PLoS ONE 7(5): e37922. doi:10.1371/journal.pone.0037922). Variants of Tn5 transposases, such as having amino acid substitutions, insertions, deletions, and/or fusions with other proteins or peptides are disclosed in U.S. Pat. Nos. 5,925, 545; 5,965,443; 7,083,980; 7,608,434; and U.S. patent application Ser. No. 14/686,961. The patents and the patent application are incorporated herein by reference in its entirety. In some embodiments, the Tn5 transposase comprise one or more substitutions at positions 54, 56, 372, 212, 214, 251, and 338 with respect to the wild type protein as disclosed in U.S. patent application Ser. No. 14/686,961. In some embodiments, the Tn5 wild-type protein or its variant can further comprise a fusion polypeptide. In some embodiments, the polypeptide domain fused to the transposase can comprise, for example, Elongation Factor Ts. Each of the references cited in this paragraph is incorporated herein by reference in its entirety.

As used herein, capture moiety includes capture probes and affinity moieties. In some embodiments, capture probes can be nucleic acids. Capture probes can associate (e.g. hybridized) with the template nucleic acids. Affinity moieties can be members of a binding pair. In some cases, the surface may comprise a first member of a binding pair and the capture probe may comprise a second member of the binding pair. In some cases, capture probes may be immobilized to the surface and the target nucleic acid may comprise a first member of a binding pair and the capture probe may comprise a second member of the binding pair. Examples of binding pair include but are not limited to biotin/streptavidin, ligand-receptor, hormone-receptor, and antigen-antibody.

In some embodiments, a transposon sequence comprises a double-stranded nucleic acid. A transposon element includes a nucleic acid molecule, or portion thereof, that includes the nucleotide sequences that form a transposome with a transposase or integrase enzyme. In some embodiments, a transposon element is capable of forming a functional complex with the transposase in a transposition reaction. Examples of transposon elements are provided herein, and include the 19-bp outer end ("OE") transposon end, inner end ("IE") transposon end, or "mosaic end" ("ME") transposon end recognized by, for example, a wild-type or mutant Tn5 transposase, or the R1 and R2 transposon end (See e.g., US Pat. App. Pub. No. 2010/0120098, which is incorporated herein by reference in its entirety). Transposon elements can comprise any nucleic acid or nucleic acid analogue suitable for forming a functional complex with the transposase or integrase enzyme in an in vitro transposition reaction. For example, the transposon end can comprise DNA, RNA, modified bases, non-natural bases, modified backbone, and can comprise nicks in one or both strands.

In some embodiments, a transposon sequence can include a transposon element and additional sequences. In some embodiments, the additional sequences can be inserted into a target nucleic acid in a transposition reaction. The additional sequences can include a primer binding site, such as a sequencing primer site and an amplification primer site. Additional sequences can also include a cleavage site, an anchor site, a reporter tag, and a barcode.

In some embodiments, a primer binding site can include sequences for sequencing primers to anneal to a nucleic acid in a sequencing reaction. In some embodiments, a primer binding site can include sequences for primers to anneal to a nucleic acid in an amplification reaction or other extension reaction.

In some embodiments, a cleavage site can include a site in a transposon sequence where breakage of a covalent bond produces two fragments. For example, a transposon sequence comprising a cleavage site can be inserted into a target nucleic acid and the modified nucleic acid can then be fragmented by bond breakage at the inserted cleavage site. In some embodiments, a cleavage site includes a restriction enzyme recognition sequence and/or a restriction enzyme cleavage site. In some embodiments, a cleavage site can include at least one ribonucleotide in a nucleic acid that may otherwise comprise deoxyribonucleotides and may be cleaved with an RNAse. Chemical cleavage agents capable of selectively cleaving the phosphodiester bond between a deoxyribonucleotide and a ribonucleotide can be used including, for example, metal ions such as rare-earth metal ions (e.g., $La^{3+}$, particularly $Tm^{3+}$, $Yb^{3+}$ or $Lu^{3+}$, Fe(3) or Cu(3)), or exposure to elevated pH. In some embodiments, a cleavage site can include one or more recognition sequences for a nickase, that is, a nicking endonuclease that breaks one strand of a double-stranded nucleic acid. Thus, the fragmentation site can include a first nickase recognition sequence, and optionally a second nickase recognition sequence. The first and second nickase recognition sequences can be the same as each other or different from each other. In some embodiments, a cleavage site can include one or more nucleotide analogues that comprise an abasic site and permits cleavage at the fragmentation site in the presence of certain chemical agents, such as polyamine, N,N'-dimethylethylenediamine (DMED) (See e.g., U.S. Pat. App. Pub. No. 2010/0022403, which is incorporated herein by reference in its entirety). In some embodiments, an abasic site may be created by modification of a uracil nucleotide within the cleavage site, for example, using a uracil DNA glycosylase (UDG) enzyme. The polynucleotide strand including the abasic site may then be cleaved at the abasic site by treatment with endonuclease (e.g. Endo IV endonuclease, AP lyase, FPG glycosylase/AP lyase, Endo VIII glycosylase/AP lyase), heat or alkali. Abasic sites may also be generated at nucleotide analogues other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease such as Endo IV or AP lyase (See e.g., U.S. 2011/0014657, which is incorporated herein by reference in its entirety). In another example, a cleavage site may include a diol linkage which permits cleavage by treatment with periodate (e.g., sodium periodate). In another example, a cleavage site may include a disulfide group which permits cleavage with a chemical reducing agent, e.g. Tris (2-carboxyethyl)-phosphate hydrochloride (TCEP). In some embodiments, a cleavage site may include a photo-cleavable moiety. Photochemical cleavage can be carried out by any of a variety of methods that utilize light energy to break covalent bonds. A site for photochemical cleavage can be provided by a non-nucleotide chemical moiety in a nucleic acid, such as phosphoramidite [4-(4,4'-dimethoxytri-tyloxy)butyramidomethyl)-1-(2-nitrophenyl)-ethyl]-2-cyanoethyl-(N,N-diisopropyl)-phosphoramidite) (Glen Research, Sterling, Va., USA, Cat No. 10-4913-XX).

In some embodiments, a transposon sequence can include an anchor site. In some embodiments, an anchor site can include sequences that can specifically bind to capture probes. In some embodiments, the anchor site comprises sequences that are complementary and/or substantially complementary to capture probes comprising nucleic acids. In some embodiments, an anchor site can include a ligand or receptor that binds a capture probe comprising a corresponding receptor or ligand. In other words, an anchor site and a capture probe can comprise a ligand/receptor pair. In some embodiments, a ligand or receptor can be associated with the anchor site of a transposon sequence through a modified nucleotide. Examples of ligands and receptors include biotin or polyHis that can bind streptavidin or nickel, respectively. Other examples include, pairs of ligands and their receptors known in the art, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC, HA, VSV-G, HSV, V5, and FLAG Tag™, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; nucleic acid strands and their complementary strands; and the like.

In some embodiments, a transposon sequence can include a reporter tag. Useful reporter tags include any of a variety of identifiable tags, labels, or groups known in the art. In certain embodiments, a reporter tag can emit a signal. Examples of signals include those that are fluorescent, chemiluminescent, bioluminescent, phosphorescent, radio-active, calorimetric, or electrochemiluminescent. Exemplary reporter tags include fluorophores, radioisotopes, chromogens, enzymes, antigens including epitope tags, semiconductor nanocrystals such as quantum dots, heavy metals, dyes, phosphorescent groups, chemiluminescent groups, electrochemical detection moieties, binding proteins, phosphors, rare earth chelates, transition metal chelates, near-infrared dyes, electrochemiluminescence labels, and mass spectrometer compatible reporter tags, such as mass tags, charge tags, and isotopes. More reporter tags that may be used with the methods and compositions described herein include spectral labels such as fluorescent dyes (e.g., fluorescein isothiocyanate, Texas red, rhodamine, and the like); radiolabels (e.g., $^3H$, $^{125}I$, $^{35}S$, $^{14}C$, $^{32}P$, $^{33}P$, etc.); enzymes (e.g., horseradish peroxidase, alkaline phosphatase etc.); spectral colorimetric labels such as colloidal gold or colored glass or plastic (e.g. polystyrene, polypropylene, latex, etc.); beads; magnetic labels; electrical labels; thermal labels; and mass tags.

In some embodiments, a transposon sequence can include a barcode. In some embodiments, a population of transposomes can include transposon sequences comprising the same barcode, one or more different barcodes, or each transposon sequence can include a different barcode. In some embodiments, a barcode inserted into a target nucleic acid can be used to identify a target nucleic acid. In some embodiments, a barcode can be used to identify an insertion event into a target nucleic acid. In some embodiments, each transposome in a population of transposomes includes a transposon sequence with a different barcode that can be used to identify an insertion site in the target nucleic acid. In some embodiments, a barcode can be used to identify the insertion site after fragmentation at a cleavage site, for example where a barcode straddles a cleavage site. Example barcodes, and methods for their preparation and use are set forth in Int. Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference in its entirety.

In some embodiments, a transposome includes two transposon sequences. In some embodiments, each transposon sequence includes a transposon element. In some embodiments, each transposon sequence can include a primer binding site, such as a sequencing primer site, and an amplification primer site, additional sequences can also include an anchor site, a reporter tag, and a barcode. Transposition of the transposon sequences into a target nucleic acid can result in cleavage of the target nucleic acid at the site of insertion. In some embodiments, the transposase of the transposome can hold on to each end of the cleaved site of the target nucleic acid, maintaining the physical proximity of cleaved fragments of a target nucleic acid.

In some embodiments, a transposon sequence can include two transposon elements that are linked to each other. A linker can be included in the insert such that a first transposon element is contiguous with a second transposon element. A particularly useful insert is one that forms a "looped" complex as set forth in Int. Pub. No. WO 2012/061832; US Pat. App. Pub. No. 2012/0208724, US Pat. App. Pub. No. 2012/0208705 and PCT App. Ser. No. PCT/US2013/031023, each of which is incorporated herein by reference in its entirety. In such structures a single insert having contiguous transposon elements binds to two transposase subunits forming a "looped" complex. The looped complex can be used to place the insert into a target nucleic acid while maintaining ordering information of the original target nucleic acid and without fragmenting the resulting modified nucleic acid polymer. Insertion of a looped transposon element provides for adding inserts into a target nucleic acid without necessarily fragmenting the target nucleic acid.

Some embodiments of the methods and compositions provided herein include the use of a substrate having a surface. In some embodiments, the surface comprises a plurality of capture probes that bind modified nucleic acids to the surface. Substrates can be two-or three-dimensional and can be a planar surface (e.g., a glass slide) or can be shaped. Useful materials include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. Suitable three-dimensional solid supports include, for example, spheres, microparticles, beads, membranes, slides, plates, micro machined chips, tubes (e.g., capillary tubes), microwells, microfluidic devices, channels, filters, or any other structure suitable for anchoring a nucleic acid or other capture probe. Solid supports can include planar micro arrays or matrices capable of having regions that include populations of nucleic acids or primers or other capture probes. Examples include nucleoside-derivatized CPG and polystyrene slides; derivatized magnetic slides; polystyrene grafted with polyethylene glycol, and the like. Various methods can be used to attach, anchor or immobilize capture probes such as nucleic acids to the surface of a solid support. The attachment can be achieved through direct or indirect bonding to the surface. The bonding can be by covalent linkage (See e.g., Joos et al. (1997) Analytical Biochemistry, 247:96-101; Oroskar et al. (1996) Clin. Chem., 42:1547-1555; and Khandjian (1986) Mol. Bio. Rep., 11:107-11, each of which is incorporated herein by reference in its entirety). A preferred attachment is direct amine bonding of a terminal nucleotide of a nucleic acid to an epoxide integrated on the surface. The bonding also can be through non-covalent linkage. For example, biotin-streptavidin (Taylor et al. (1991) 1. Phys. D: Appl. Phys., 24:1443, which is incorporated herein by reference in its entirety) and digoxigenin with anti-digoxigenin (Smith et al., Science, 253: 1122 (1992), which is incorporated herein by reference in its entirety) are common tools for anchoring nucleic acids to surfaces. Attachment of a nucleic acid to a surface can be via an intermediate structure such as a bead, particle or gel. Attachment of nucleic acids to an array via a gel is exemplified by flow cells available commercially from Illumina Inc. (San Diego, Calif.) or described in US Pat. App. Pub. No. 2010/10111768; U.S. Pat. App. Pub. No. 2012/0270305; and U.S. Pat. No. 8,563,477, each of which is incorporated herein by reference in its entirety.

In some embodiments, a capture probe can include a nucleic acid complementary or substantially complementary to an anchor sequence, a receptor or ligand as provided herein. In some embodiments, a capture probe comprises a recombinase that binds regions of double-stranded nucleic acids comprising non-complementary strands, such as "bubbles" in a double stranded nucleic acid.

In some embodiments, a substrate can have a continuous or monolithic surface. Thus, nucleic acid fragments can attach at spatially random locations wherein the distance between nearest neighbor fragments (or nearest neighbor clusters derived from the fragments) will be variable. The resulting arrays can have a variable or random spatial pattern of features. In some embodiments, a substrate used in a method set forth herein can include an array of capture probes that are present in a repeating pattern. In some such embodiments, the capture probes provide the locations to which nucleic acids can attach. In some embodiments, repeating patterns are hexagonal patterns, rectilinear patterns, grid patterns, patterns having reflective symmetry, patterns having rotational symmetry, or the like. The capture probes to which a modified nucleic acid attach can each have an area that is, or is smaller than, about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$, or a range defined by any two of the preceding values. Alternatively or additionally, each feature can have an area that is, or is larger than, about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$, or a range defined by any two of the preceding values. A cluster or colony of nucleic acids that result from amplification of fragments on an array (whether patterned or spatially random) can similarly have an area that is in a range above or between an upper and lower limit selected from those exemplified above.

Several commercially available sequencing platforms rely on substrates having wells that provide a barrier to the diffusion of detection reagents (e.g. pyrophosphate in platforms available from 454 LifeSciences (a subsidiary of Roche, Basel Switzerland) or protons in platforms available from Ion Torrent (a subsidiary of Life Technologies, Carlsbad Calif.)) during sequence detection steps.

Some embodiments provided herein include amplifying portions of a target nucleic acid, modified nucleic acid, or fragments thereof. Any suitable amplification methodology known in the art can be used. In some embodiments, nucleic acid fragments are amplified on a solid support. For example, in some embodiments, the nucleic acid fragments are amplified using bridge amplification methodologies as exemplified by the disclosures of U.S. Pat. No. 5,641,658; U.S. Patent Publ. No. 2002/0055100; U.S. Pat. No. 7,115,400; U.S. Patent Publ. No. 2004/0096853; 10 U.S. Patent Publ. No. 2004/0002090; U.S. Patent Publ. No. 2007/0128624; and U.S. Patent Publ. No. 2008/0009420, each of which is incorporated herein by reference in its entirety.

Bridge amplification methods allow amplification products to be immobilized on a solid support in order to form arrays comprised of clusters (or "colonies") of immobilized nucleic acid molecules. Each cluster or colony on such an array is formed from a plurality of identical immobilized polynucleotide strands and a plurality of identical immobilized complementary polynucleotide strands. The arrays so-formed can be referred to herein as "clustered arrays". The products of solid-phase amplification reactions are so-called "bridged" structures when formed by annealed pairs of immobilized polynucleotide strands and immobilized complementary strands, both strands being immobilized on the solid support at the 5' end, preferably via a covalent attachment. Bridge amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR, solid-phase MDA, solid-phase RCA etc. whether one or both primers of each pair of amplification primers are immobilized.

It will be appreciated that any of the amplification methodologies described herein or generally known in the art can be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference in its entirety) and oligonucleotide ligation assay (OLA) (See e.g., U.S. Pat. Nos. 7,582,420, 5,185,243, 5,679,524 and 5,573,907; EP 0320308; EP 0336731; EP 0439182; WO 90101069; WO 89/12696; and WO 89109835, each of which is incorporated herein by reference in its entirety). It will be appreciated that these amplification methodologies can be designed to amplify immobilized nucleic acid fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the GoldenGate assay (Illumina, Inc., San Diego, Calif.) as exemplified by U.S. Pat. Nos. 7,582,420 and 7,611,869, each of which is incorporated herein by reference in its entirety.

An isothermal amplification technique can be used in a method of the present disclosure. Exemplary isothermal amplification methods include, but are not limited to, Multiple Displacement Amplification (MDA) as exemplified by, for example, Dean et al., Proc. Natl. Acad. Sci. USA 99:5261-66 (2002) or isothermal strand displacement nucleic acid amplification as exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., *Molecular Methods for Virus Detection*, Academic Press, Inc., 1995; U.S. Pat. Nos. 5,455,166, and 5,130,238, and Walker et al., *Nucl. Acids Res.* 20:1691-96 (1992) or hyperbranched strand displacement amplification which is described in, for example Lage et al., *Genome Research* 13:294-307 (2003), each of which is incorporated herein by reference in its entirety.

Additional description of amplification reactions, conditions and components are set forth in U.S. Pat. No. 7,670,810, which is incorporated herein by reference in its entirety. Other useful isothermal amplification techniques include recombinase-facilitated amplification techniques such as those sold commercially as TwistAmp™ kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference in its entirety. Helicase dependent amplification can also be used, for example, as described in Xu et al. EMBO Rep 5:795-800 (2004), which is incorporated herein by reference in its entirety. Conditions that achieve kinetic exclusion amplification can be particularly useful and are described, for example, in US 2013/0338042, which is incorporated herein by reference in its entirety.

In some embodiments, it may be desirable to perform a re-seeding step. For example, modified nucleic acid fragments can be captured at locations within a region of a surface, replicated on one or more cycles of an amplification process, the original fragments and/or amplicons thereof can be released from the locations, the released nucleic acids can be captured at other locations in the same region, and the newly captured nucleic acids can be amplified. In one embodiment, modified nucleic acid fragments are copied through first extension prior to reseeding, and recaptured at a different location which can be in close proximity to the first capture point or even far away from it. In a specific example, a single cycle of bridge amplification can be carried out for a fragment that was seeded on a surface and instead of washing away the original template fragment upon release from the surface, the template fragment can re-seed the surface at a new location that is proximal to the location where it had originally seeded. Subsequent rounds of bridge amplification will allow cluster growth at both the original seed location and at the re-seed location. Using such methods replicate colonies can be created at a region of a surface to provide technical replicates. In some embodiments of the above example, the transposon sequences may comprise unique molecular identifiers (UMI). The UMI will allow tracking the library molecules and will be able to determine that the clusters that share the same UMI (and genomic sequences) were derived from the same original library molecule. Analysis of the sequences for the technical replicates can provide the benefit of error checking. For example, observed sequence variants that occur in only a subset of proximal clusters (that are identified as technical replicates) can be identified as amplification errors, whereas sequence variants that occur in all clusters that are identified as technical replicates for a particular fragment are more likely to be true variants.

Some embodiments of the methods described herein can include a step of sequencing fragments derived from a target nucleic acid. One example is sequencing-by-synthesis (SBS). In SBS, extension of a nucleic acid primer along a nucleic acid template (e.g. a fragment of a target nucleic acid or amplicon thereof) is monitored to determine the sequence of nucleotides in the template. The primer can hybridize to a priming site that is present in an insert as set forth above. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array using steps set forth herein can be subjected to an SBS technique under conditions where events occurring for different templates can be distinguished due to their location in the array.

In some embodiments, flow cells provide a convenient format for housing an array of nucleic acid fragments that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid fragments. Those sites of an array where primer extension (e.g. via hybridization of the primer to a priming site located on an insert attached to a nucleic acid fragment) causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated "n" times to extend the primer by n nucleotides, thereby detecting a sequence of length "n". Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 071123744; U.S. Pat. Nos. 7,329,492; 7,211, 414; 7,315,019; 7,405,281, and US Pat. App. Pub. No. 2008/0108082, each of which is incorporated herein by reference in its entirety.

In some embodiments, other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference in its entirety). In pyrosequencing, released PPi can be detected by being converted to adenosine triphosphate (ATP) by ATP sulfurylase, and the level of ATP generated can be detected via luciferase produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to methods of the present disclosure are described, for example, in WO 2012058096, US Pat. App. Pub. No. 2005/0191698, U.S. Pat. Nos. 7,595,883, and 7,244,559, each of which is incorporated herein by reference in its entirety. Sequencing-by-ligation reactions are also useful including, for example, those described in Shendure et al. Science 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989110977, each of which is incorporated herein by reference in its entirety.

In some embodiments, such as sequencing-by-ligation and sequencing-by-hybridization procedures, target nucleic acid fragments (or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and y-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); and Korlach et al. *Proc. Natl. Acad. Sci. USA* 105, 1176-1181 (2008), the disclosures of which are incorporated herein by reference in their entireties.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. No. 2009/10026082 AI; US Pat. App. Pub. No. 2009/10127589 AI; US Pat. App. Pub. No. 2010/10137143; or US Pat. App. Pub. No. 2010/10282617, each of which is incorporated herein by reference in its entirety.

In some embodiments, a sequencing step of the present methods can include a nanopore sequencing technique such as those described in Deamer & Akeson *Trends Biotechnol.* 18, 147-151 (2000); Deamer & Branton, *Acc. Chem. Res.* 35:817-825 (2002); and Li et al., *Nat. Mater.* 2:611-615 (2003), each of which is incorporated herein by reference in its entirety. In such embodiments, the target nucleic acid fragment passes through a nanopore. The nanopore can be a synthetic pore or biological membrane protein, such as alpha-hemolysin. As the target nucleic acid passes through the nanopore, each base can be identified by measuring fluctuations in the electrical conductance of the pore. (U.S. Pat. No. 7,001,792; Soni & Meller *Clin. Chem.* 53, 1996-2001 (2007); *Healy, Nanomed.* 2:459-481 (2007); and Cockroft et al., *J. Am. Chem. Soc.* 130:818-820 (2008), each of which is incorporated herein by reference in its entirety). In some embodiments, the location of individual nanopores is akin to a site or feature on the arrays exemplified herein. The proximity of nanopores to each other can be correlated with the proximity of fragment sequences they read, for example, to facilitate assembly of those fragments into the larger sequence from which they were derived.

In some embodiments, the sequencing steps described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface bound target nucleic acids, or fragments thereof, the target nucleic acids, or fragments, can be in an array format. In an array format, fragments of target nucleic acids can be typically coupled to a surface in a spatially distinguishable manner, for example, using attachment techniques set forth herein. The array can include a single copy of a target nucleic acid fragment at each site (also referred to as a feature) or multiple copies having the same sequence can be present at each site or feature. Multiple copies can be produced by amplification methods such as, bridge amplification or emulsion PCR.

Preparation of Template Nucleic Acids

Some embodiments of the methods provided herein include preparing a template nucleic acid for sequencing in contact with a substrate, such as a flow cell. In some embodiments, a target nucleic acid is modified by insertion of transposon sequences; the modified nucleic acid is fragmented by the insertion of the transposon sequences or by a subsequent cleavage step; additional sequences may be added to one or more ends of the fragmented nucleic acid fragments by amplification with tailed-primers or ligation with primers; the fragments are captured by capture probes on the surface; the captured fragments may be amplified by bridge amplification; and the captured fragments are sequenced on the surface. In some embodiments, the nucleic acids for sequencing are prepared in situ in a reaction volume in contact with the surface.

Some embodiments of the methods provided herein include (a) providing a substrate having a surface comprising a plurality of capture probes attached thereto; (b) contacting the surface with a reaction volume comprising a plurality of template nucleic acids and transposomes, each transposome comprising a transposon sequence and the transposase; wherein the template nucleic acids are prepared by contacting a target nucleic acid with a plurality of transposomes, and (c) associating the template nucleic acids with the capture probes. Some embodiments also include (d) sequencing the associated template nucleic acids.

In some embodiments, the substrate is a flow cell having a surface comprising capture probes such as P7 and P5 sequences or sequences complementary thereto attached to the surface. P7 and P5 probes are described, for example, in U.S. Pat. No. 8,563,477 and Bentley et al., Nature 456:53-59 (2008), each of which is incorporated herein by reference in its entirety. In some embodiments, the reaction volume comprises a target nucleic acid, a plurality of transposomes comprising transposon sequences. Transposomes useful with the methods provided herein are described herein.

In some embodiments, the reaction volume comprises a plurality of nucleic acid fragments of a target nucleic acid, the nucleic acid fragments comprising transposon sequences, and a plurality of transposomes. In some embodiments, the reaction volume also includes a ligase, a polymerase, dNTPs and/or primers to amplify the nucleic acid fragments or to ligate additional sequences to the nucleic acid fragments. In some embodiments, insertion of transposon sequences into the target nucleic acid occurs when the reaction volume is in contact with the substrate.

In some embodiments insertion of transposon sequences into the target nucleic acid occurs before the reaction volume contacts with the substrate. In some embodiments, a plurality of reaction volumes can be prepared, each reaction volume comprising a different target nucleic acid. Each target nucleic acid can be identified based on a barcode that is attached to the nucleic acid by a transposome comprising transposon sequences comprising the barcode. Thus, individual nucleic acids in a plurality of nucleic acids can be treated with a plurality of transposomes having a set of transposons with different barcodes such that the individual nucleic acids are identifiable by a unique barcode that is attached to it by a transposome.

In some embodiments, a transposome includes two transposon sequences in which each transposon sequence includes a transposon element. In some embodiments, one or more of the two transposon sequences includes a primer binding site, an anchor site, and/or a barcode. In some embodiments, the transposon sequence comprises P7 and P5 sequences or sequences complementary thereto.

In some embodiments, insertion of transposon sequences into a double-stranded target nucleic acid produces a modified double-stranded nucleic acid with single-stranded gaps. In some embodiments, the single-stranded gaps are filled-in with use of a polymerase and/or ligase.

In some embodiments, the nucleic acid fragments are amplified with tailed-primers. Amplification with the tailed-primers results in the addition of sequences to one or more ends of the amplified nucleic acid fragments. In some embodiments, the additional sequences can include a primer binding site, and/or an anchor site.

In some embodiments, the double-stranded nucleic acid fragments are melted to single-stranded fragments. The single stranded nucleic acid fragments can be used in one or more steps of a method set forth herein.

In some embodiments, the nucleic acid fragments or the amplified nucleic acids fragments are captured through the anchor sites by the capture probes. In some embodiments, the anchor sites are nucleic acids that capture the fragments via hybridization of complementary sequences on the probes and fragments. For example, hybridization can be mediated by anchor sites or capture probes that comprise P7 and P5 sequences or sequences complementary thereto.

In some embodiments, the captured nucleic acids are amplified. In some embodiments, the amplification is bridge amplification. Alternatively or additionally, other amplification methods set forth herein can be used In some embodiments, the captured nucleic acids are sequenced on the surface, for example, using methods set forth herein.

Obtaining Haplotype Information

Target nucleic acids such as genomic DNA can include more than a single haplotype. For example, human genomic DNA, contains two sets of DNA molecules, each set with a different combination of maternal and paternal sequences. Some embodiments provided herein are useful to obtain sequence information from fragments of a single nucleic acid molecule or copies thereof. Further information can be obtained about the haplotype structure or phase of the sequences. An advantage of the methods is the ability to determine haplotypes or phases for a region of sequence in a target nucleic acid that is larger than the fragments of the target nucleic acid that are physically sequenced.

In some embodiments, the physical proximity of certain fragments on the substrate is maintained. In some embodiments, the sequences of fragments that have a closer proximity to one another in the sequence of the linear target nucleic acid have a closer physical proximity to one another on the surface compared to sequences of fragments that are less proximate from each other in the sequence of the linear target nucleic acid. The physical proximity of the fragments can be used to determine the proximity of the fragment sequences in a representation of the target sequence from which the fragments were derived. The physical proximity of certain fragments can be retained by a variety of methods.

In some embodiments, a target nucleic acid is fragmented by insertion of transposon sequences. However, in other embodiments the presence of the transposase can keep the two fragments together, for example, as described in U.S. Pat. App. Ser. No. 61/919,529, which is incorporated herein by reference in its entirety. In some embodiments, the transposase can be removed after the fragments are captured on the surface. In some embodiments, the reaction volume can include an agent to reduce diffusion of fragments such that proximate fragments of the target nucleic acid remain in close proximity.

In some embodiments, methods to obtain haplotype information include comparing complementary sequences determined for proximal locations on the surface to identify sequence errors. In some embodiments, the relative proximity of any two fragment species on the surface can provide information useful for alignment of sequence information obtained from the two fragments. Specifically, the distance between clusters, derived from any two given fragments, on the surface can be positively correlated with the probability that the two clusters are from the same target polynucleotide molecule, as described in greater detail in WO 2012/025250, U.S. Pat. App. Ser. No. 61/919,529 and U.S. patent application Ser. No. 13/790,220, each of which is incorporated herein by reference in its entirety.

As an example, in some embodiments, fragments derived from a long nucleic acid molecule captured at the surface of a flow cell occur in a line across the surface of the flow cell (e.g. if the nucleic acid was stretched out prior to fragmentation or amplification) or in a cloud on the surface. Further, a physical map of the immobilized nucleic acid can then be generated. The physical map thus correlates the physical relationship of clusters after the immobilized nucleic acid is amplified. Specifically, the physical map is used to calculate the probability that sequence data obtained from any two clusters are linked, as described in the incorporated materials of WO 2012/025250, U.S. Pat. App. Ser. No. 61/919,529 and U.S. patent application Ser. No. 13/790,220, each of which is incorporated herein by reference in its entirety.

In some embodiments, the physical map is generated by imaging the surface to establish the location of the immobilized nucleic acid molecules across the surface. In some embodiments, the immobilized nucleic acid is imaged by adding an imaging agent to the solid support and detecting a signal from the imaging agent. In some embodiments, the imaging agent is a detectable label. Suitable detectable labels, include, but are not limited to, protons, haptens, radionuclides, enzymes, fluorescent labels, chemiluminescent labels, and/or chromogenic agents. For example, in some embodiments, the imaging agent is an intercalating dye or non-intercalating DNA binding agent. Any suitable intercalating dye or non-intercalating DNA binding agent as are known in the art can be used, including, but not limited to those set forth in U.S. Pat. App. Pub. No. 2012/0282617, which is incorporated herein by reference in its entirety.

In certain embodiments, a plurality of modified nucleic acid molecules is flowed onto a flow cell comprising a plurality of nano-channels. As used herein, the term nano-channel refers to a narrow channel into which nucleic acid molecules can be delivered. The delivery can involve stretching the nucleic acid molecules in a direction along the length of the channel. In some embodiments, the number of strands is, or is no more than 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900 or 1000 individual long strands of nucleic acid, or a range defined by any two of the preceding values, that are stretched across each nano-channel. In some embodiments the individual nano-channels are separated by a physical barrier that prevents individual long strands of target nucleic acid from interacting with multiple nano-channels. In some embodiments, the solid support comprises, or comprises at least, 10, 50, 100, 200, 500, 1000, 3000, 5000, 10000, 30000, 50000, 80000 or 100000 nano-channels, or a range defined by any two of the preceding values.

In some embodiments, the nucleic acids have been modified to include inserts having cleavage sites and the cleavage sites are cleaved once the nucleic acids have been delivered to the channel (e.g. via stretching along the channel). The resulting fragments can be optionally amplified to form clusters along the surface of the channel. Contiguity mapping can then be performed, for example, by following the clusters down the length of one of these channels or otherwise accounting for proximity of the clusters on the surface of the channel. As an example, a flow cell having 1000 or more nano-channels with mapped immobilized fragmentation products in the nano-channels can be used to sequence the genome of an organism with short 'positioned' reads. In some embodiments, mapped immobilized fragmentation products in the nano-channels can be used to resolve haplotypes. In some embodiments, mapped immobilized fragmentation products in the nano-channels can be used to resolve phasing issues.

Reaction Vessels

Some embodiments of the methods and compositions provided herein include a reaction vessel for sequencing a target nucleic acid. In some embodiments, a reaction vessel can include a substrate comprising a surface having a plurality of capture probes attached thereto; and a reaction volume in fluid communication with the surface comprising: a transposase, a plurality of template nucleic acids prepared by contacting a target nucleic acid with a plurality of transposomes, each transposome comprising a transposon sequence and the transposase, and a polymerase and dNTPs or ligase. In some embodiments, the target nucleic acids fragmented by transposomes are extended for at least one base with a polymerase prior to ligation. In some embodiments, a flow cell includes the reaction vessel. In some embodiments, the reaction vessel can include a channel and/or a well of the flow cell.

In some embodiments, the capture probes are patterned on the surface. In some embodiments, the capture probes are restricted to sites on the surface.

In some embodiments, the reaction volume comprises a liquid (e.g. an aqueous liquid having a pH buffer) configured for reaction steps comprising: transposing the transposon sequences into the target nucleic acid; extending the template nucleic acids with the polymerase followed by ligation; and associating the template nucleic acids with the capture probes. In some embodiments, the liquid is configured for a reaction step comprising removing the transposase in the presence of a protease or SDS. In some embodiments, the liquid is configured for associating the template nucleic acids with the capture probes in the presence of a recombinase. In some embodiments, the liquid is configured for amplifying the template nucleic acids associated with the capture probes. In some embodiments, the amplification is bridge amplification. In some embodiments, the reaction volume comprises reagents for transposing the transposon sequences into the target nucleic acid; extending the template nucleic acids with the polymerase and/or ligase; and associating the template nucleic acids with the capture probes. In some embodiments, the reaction volume comprises reagents for removing the transposase in the presence of a protease or SDS. In some embodiments, the reaction volume comprises reagents for associating the template nucleic acids with the capture probes in the presence of a recombinase. In some embodiments, the reaction volume comprises reagents for amplifying the template nucleic acids associated with the capture probes.

In some embodiments, the template nucleic acids are associated with the capture probes. In some embodiments, the capture probes comprise nucleic acids. In some embodiments, the template nucleic acids are hybridized to the capture probe. In some embodiments, at least one of the template nucleic acids, at least one of the capture probes, and/or the surface each comprise an affinity moiety. In some embodiments, the affinity moiety is selected from the group consisting of biotin, avidin, and streptavidin. In some embodiments, the capture probes comprise a recombinase. In some embodiments, the affinity moiety of at least one of the template nucleic acids is attached to the affinity moiety of at least one of the capture probe or to the affinity moiety of the surface.

In some embodiments, the transposase is selected from the group consisting of Tn5, variant of Tn5, hyperactive Tn5, Tn10, and Mu. In some embodiments, the transposon sequence comprises a sequence selected from the group consisting of a barcode, a sequencing primer, and a fragmentation site. In some embodiments, the transposome comprises two transposon sequences. In some embodiments, the transposon sequences are different.

In some embodiments, the target nucleic acid is selected from the group consisting of DNA and RNA. In some embodiments, the target nucleic acid is selected from the group consisting of genomic DNA and cDNA. In some embodiments the target nucleic acid is genomic DNA.

In some embodiments, the surface comprises, or comprises at least about 10,000 template nucleic acids per $mm^2$, at least about 100,000 template nucleic acids per $mm^2$, at least about 1,000,000 template nucleic acids per $mm^2$.

In some embodiments, the proximity of sequence information obtained from two template nucleic acids in a linear representation of the target nucleic acid sequence is used to determine the proximity of the template nucleic acids on the surface. In some embodiments, template nucleic acids in closer proximity to one another on the surface are determined to comprise sequences in closer proximity in a representation of the target nucleic acid sequence compared to template nucleic acids in less close proximity. In some embodiments, the representation of the target nucleic acid sequence comprises haplotype or phasing information.

Some embodiments of the methods and compositions provided herein include a system for sequencing a target nucleic acid comprising a reaction vessel provided herein, a thermocycler for modulating the temperature of the reaction vessel; and a detector for collecting signals from the reaction vessel.

Some embodiments also include a processor comprising instructions to modulate the temperature of the reaction vessel to perform steps comprising: transposing the transposon sequences into the target nucleic acid, extending the template nucleic acids with the polymerase or a combination of polymerase and ligase, and associating the template nucleic acids with the capture probes or to the capture moiety of a surface. In some embodiments, the instructions to modulate the temperature of the reaction vessel to perform steps comprise amplifying the template nucleic acids associated with the capture probes. In some embodiments, the amplification is bridge amplification.

EXAMPLES

Example 1—Automated Library Preparation on a Flow Cell

The following example demonstrates an embodiment of an automated preparation of a transpositional library and sequencing of the library on a flow cell.

Unsheared genomic DNA was isolated from E. coli. Several reaction volumes were prepared with various amounts of the DNA with 31.25 µl tagmentation solution (25 µl 2× Illumina Tagment DNA Buffer; 5 µl Tn5 transposomes; 0.25 µl Taq DNA polymerase; and 1 µl 10 mM dNTPs) in a total volume of 50 µl. The various amounts of DNA included: 2 µg, 1 µg, 0.5 µg, 0.3 µg, 0.1 µg, 0.05 µg and 0.02 µg. Each reaction volume was loaded on to a flow cell by using a cBOT instrument (Illumina, Inc., San Diego, Calif.).

The initial temperature of the flow cell was set at 20° C., and all temperature changes described were performed at a ramp rate of 1° C./s. Firstly, 160 µl wash buffer was flowed across each lane of the flow cell at 60 µl/minute; and 20 µl air was pumped inside each inlet tube at 60 µl/minute.

Each 50 µl reaction volume was pumped into the respective flow cell lane followed by 25 µl air to push the reaction solutions inside the lanes on the flow cell. The temperature of the flow cell was increased to 55° C. and then incubated for 5 minutes; 60° C. for 1 minute; 65° C.; for 1 minute; 70° C. for 1 minute; and 74° C. for 1 minute. To denature double-stranded DNA products to single-stranded DNA, the flow cell was heated to 94° C. for 5 minutes. To permit hybridization of the single-stranded DNA to surface capture oligonucleotides immobilized on the surface of the flow cell, the temperature of the flow cell was lowered to 40° C. for 5 minutes. To copy the hybridized DNA molecules by extension of the capture oligonucleotides, the temperature of the flow cell was raised to 74° C. for 1.5 minutes. To wash the reaction solution from the flow cell lanes, the flow cell temperature was lowered to 60° C. and 160 µl of wash buffer was flowed across each lane of the flow cell at 60 µl/min.

The immobilized DNA templates were amplified with 28 cycles of isothermal bridge amplification. Each double stranded cluster was linearized, the linearized P5 strand was removed with 0.1M NaOH, the reverse strand removed by specific base cleavage, leaving the forward strand. The sequencing primer was hybridized to the complementary sequence on the adapter on the 3' ends of the templates in the clusters. Sequencing was performed on a GAIIx Genome Analyzer (Illumina, Inc. San Diego, Calif.) for paired end sequencing for 36 cycles of sequence by synthesis sequencing reads.

Figure 2A:
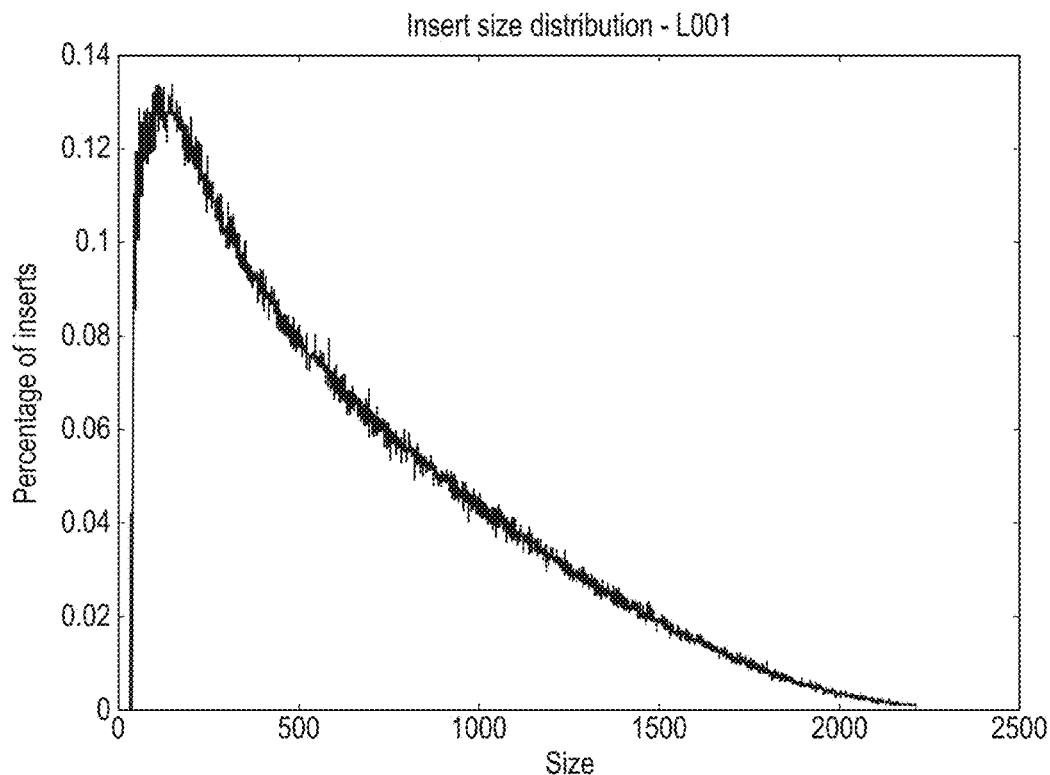
FIG. 2A, FIG. 2B, and FIG. 2C show graphs for gap size distribution of clusters with FIG. 2A, FIG. 2B and FIG. 2C showing results from lanes 1, 2, and 3, respectively. X-axis is size of insert in bp, and y-axis is percentage of inserts.
Figure 2B:
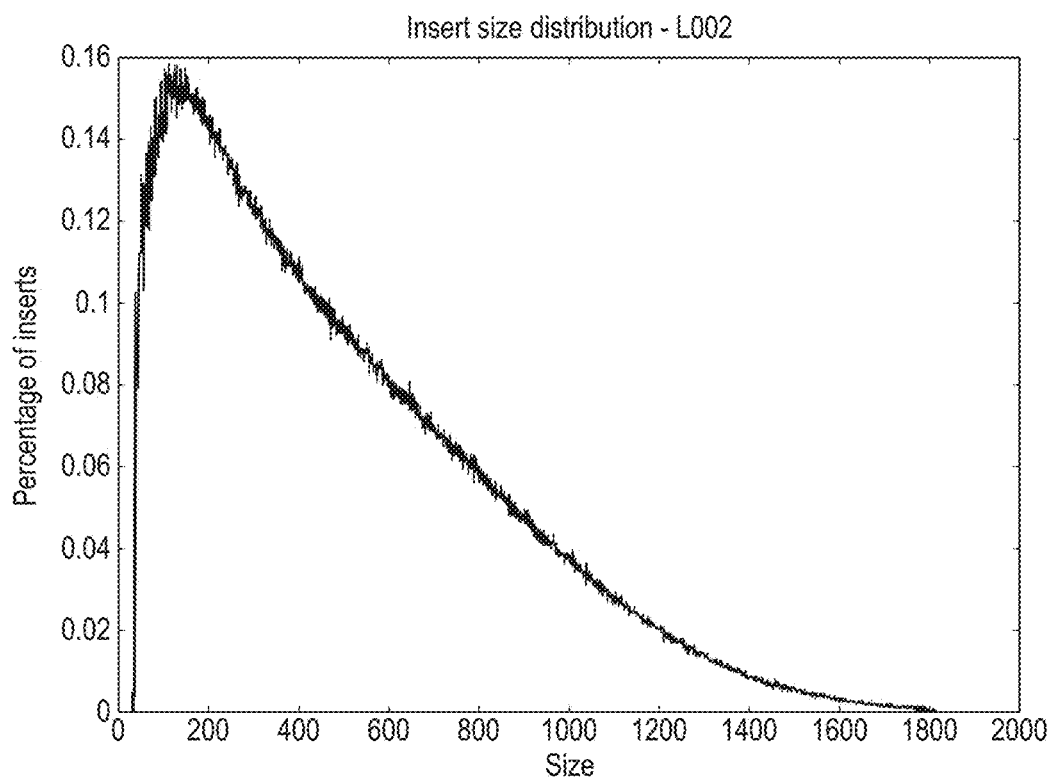
Figure 2C:
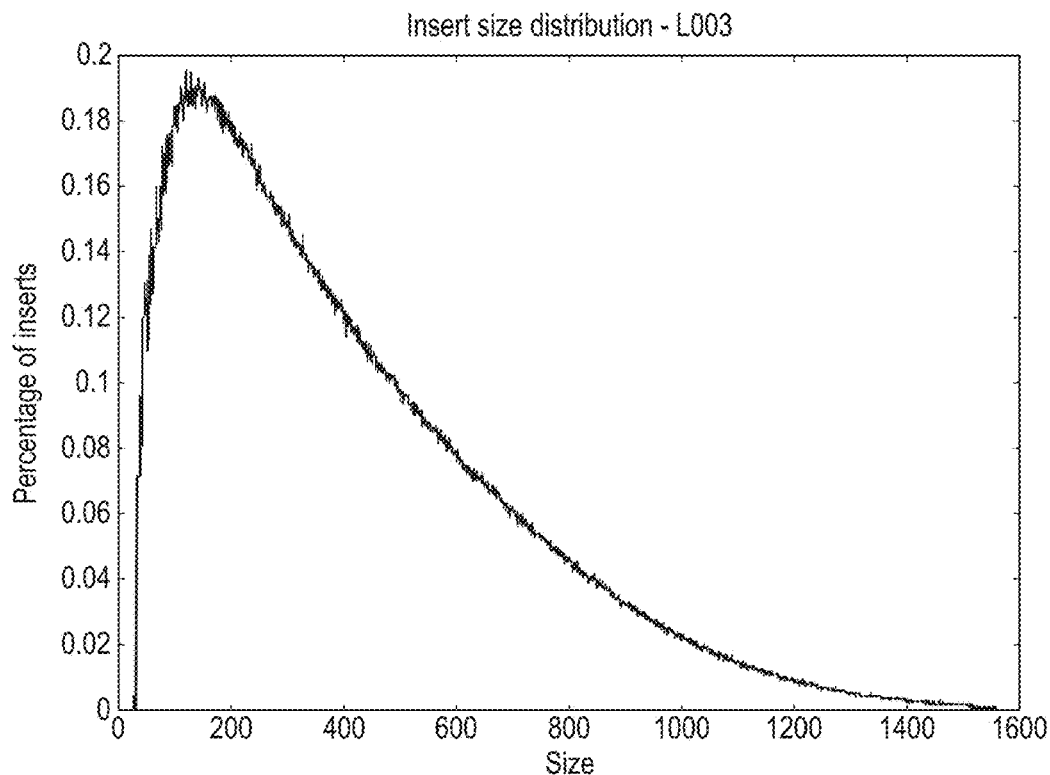
Figure 3A:
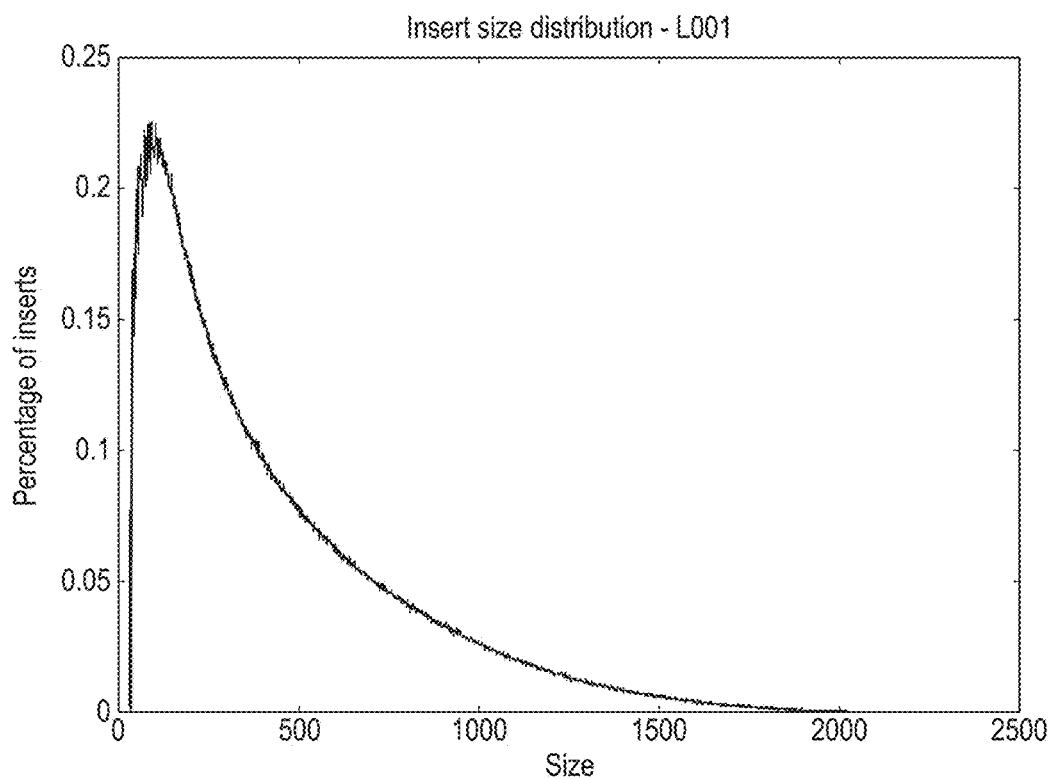
FIG. 3A, FIG. 3B, FIG. 3C, and FIG. 3D show graphs for gap size distribution for inserts for samples from genomic DNA from *E. coli*, human, *Rhodobacter*, and *Bacillus cereus*, respectively.
Figure 3B:
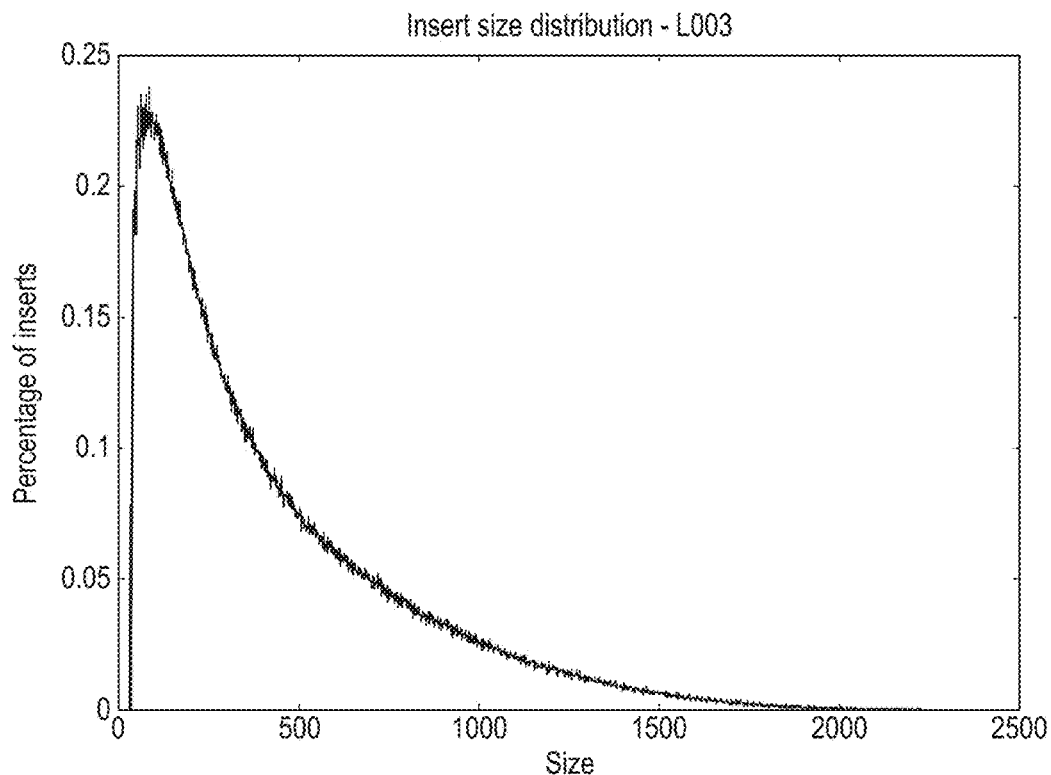
Figure 3C:
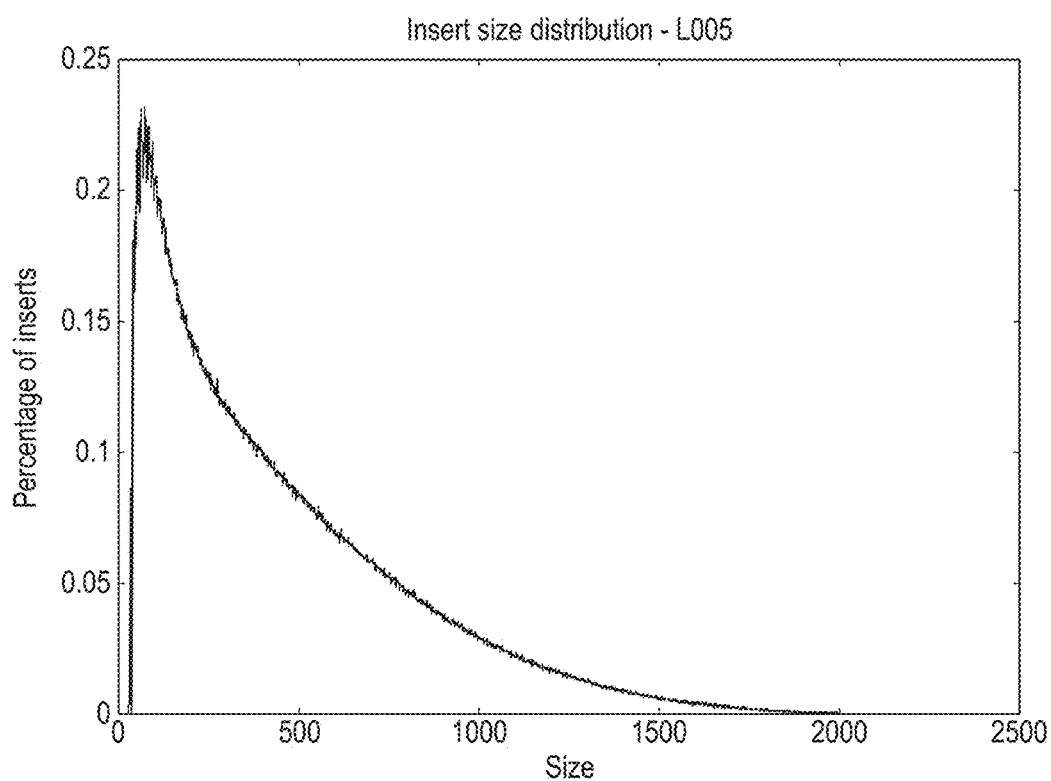
Figure 3D:
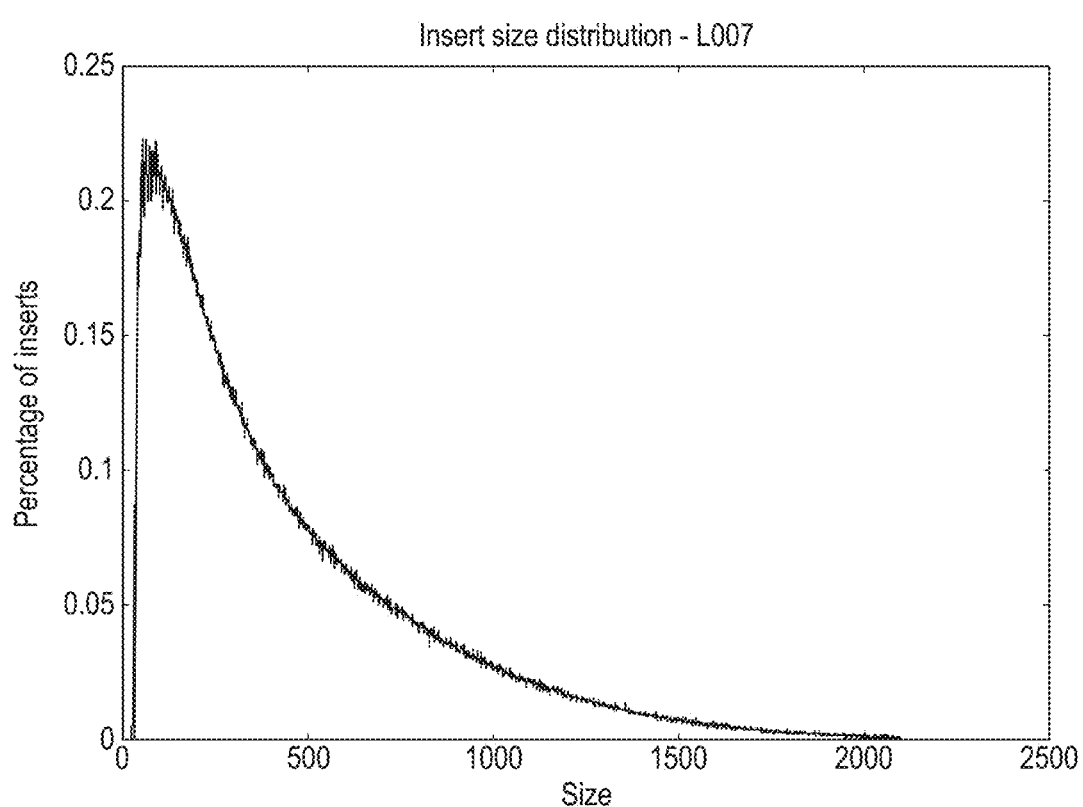

Table 1 shows sequencing metrics including cluster densities up to about 700 k/$mm^2$ and clusters having acceptable levels of Cluster passing filter (PF) and good quality scores (%>=Q30). An inverse correlation between cluster density and amount of genomic DNA used was observed. TABLE 2 summarizes the results and shows that about 93% of clusters aligned successfully with an E. coli reference genome. Longer inserts were obtained with larger amounts of genomic DNA. FIGS. 2A-C includes graphs for insert size distribution for lanes 1, 2, and 3, respectively.

TABLE 1

| Lane | DNA (μg) | Tiles | Density (k/mm²) | Cluster PF (%) | Phas/Prepas (%) | Reads (M) | Reads PF (M) | % >= Q30 | Yield (G) |
|---|---|---|---|---|---|---|---|---|---|
| 1 | 2 | 22 | 209 +/− 3 | 91.52 +/− 0.77 | 0.097/0.150 | 2.50 | 2.29 | 98.0 | 0.1 |
| 2 | 1 | 22 | 425 +/− 13 | 88.04 +/− 0.92 | 0.125/0.154 | 5.08 | 4.47 | 97.3 | 0.2 |
| 3 | 0.5 | 22 | 604 +/− 17 | 87.08 +/− 0.64 | 0.134/0.146 | 7.23 | 6.29 | 96.6 | 0.2 |
| 4 | 0.3 | 22 | 704 +/− 1.06 | 84.54 +/− 1.06 | 0.138/0.149 | 8.42 | 7.12 | 95.7 | 0.2 |

TABLE 2

| Lane | Sample yield (Mbases) | Cluster (raw) | Clusters (PF) | 1$^{st}$ cycle int (PF) | % PF clusters | % Align (PF) | % mismatch rate (PF) |
|---|---|---|---|---|---|---|---|
| 1 | 80 | 2501569 | 2289541 | 218 | 91.52 | 92.37 | 0.11 |
| 2 | 157 | 5080310 | 4473291 | 225 | 88.05 | 93.43 | 0.06 |
| 3 | 220 | 7225510 | 6291501 | 234 | 87.07 | 93.99 | 0.06 |
| 4 | 249 | 8423813 | 7120560 | 238 | 84.53 | 93.33 | 0.06 |

Example 2—Library Preparation from Various Genomic DNA Sources

In the embodiment of this example, transpositional libraries were prepared from genomic DNA from various organisms and sequenced. This example includes Materials and methods for automated sample prep experiment with HiSeq flow cell C3F68ACXX (Illumina Inc., San Diego, Calif.)

Stock solutions of 50 ng/μl genomic DNA were prepared from various organisms including E. coli, human, Rhodobacter, and Bacillus cereus. Rhodobacter has a relatively GC-rich genome, and Bacillus cereus has a relatively AT-rich genome. A tagmentation solution was prepared by mixing the following components: 132 μl H$_2$O; 88 μl 5× Nextera reaction buffer; 8.8 μl of 10 mM dNTPs; 2.2 μl Taq DNA polymerase (5 U/μl); and 44 μl transposomes. 50 μl reaction volumes were prepared with 31.25 μl of tagmentation solution and 300 ng or 500 ng genomic DNA. Each reaction volume was mixed and transferred to a lane on a HiSeq flow cell (Illumina Inc., San Diego, Calif.) using a cBOT instrument (Illumina Inc., San Diego, Calif.). The tagmentation and bridge amplification reactions were performed under the conditions in TABLE 3.

TABLE 3

| Step | Rate of temperature change (° C./second) | Flow rate (μl/min) | Volume (μl) |
|---|---|---|---|
| Incubate at 20° C. | 0.9 | | |
| Pump wash buffer | | 60 | 80 |
| Pump air | | 60 | 10 |
| Pump tagmentation reaction | | 60 | 40 |

TABLE 3-continued

| Step | Rate of temperature change (° C./second) | Flow rate (μl/min) | Volume (μl) |
|---|---|---|---|
| Pump air | | 60 | 40 |
| Incubate at 55° C. for 5 minutes | 0.9 | | |
| Incubate at 60° C. for 1 minute | 0.9 | | |
| Incubate at 65° C. for 1 minute | 0.9 | | |
| Incubate at 70° C. for 1 minute | 0.9 | | |
| Incubate at 74° C. for 1 minute | 0.9 | | |
| Incubate at 94° C. for 5 minutes | 0.9 | | |
| Incubate at 74° C. for 1.5 minutes | 0.9 | | |
| Go to 60° C. | 0.9 | | |
| Pump wash buffer | | 60 | 120 |
| Perform 28 cycles of isothermal amplification | | 30 | |

Sequencing data was obtained. TABLE 4 and TABLE 5 each show sequencing metrics for a tile from some of the lanes on the flow cell. FIGS. 3A, 3B, 3C, and 3D show gap size distribution for inserts for samples from genomic DNA from E. coli, human, Rhodobacter, and Bacillus cereus, respectively.

Figure 4:
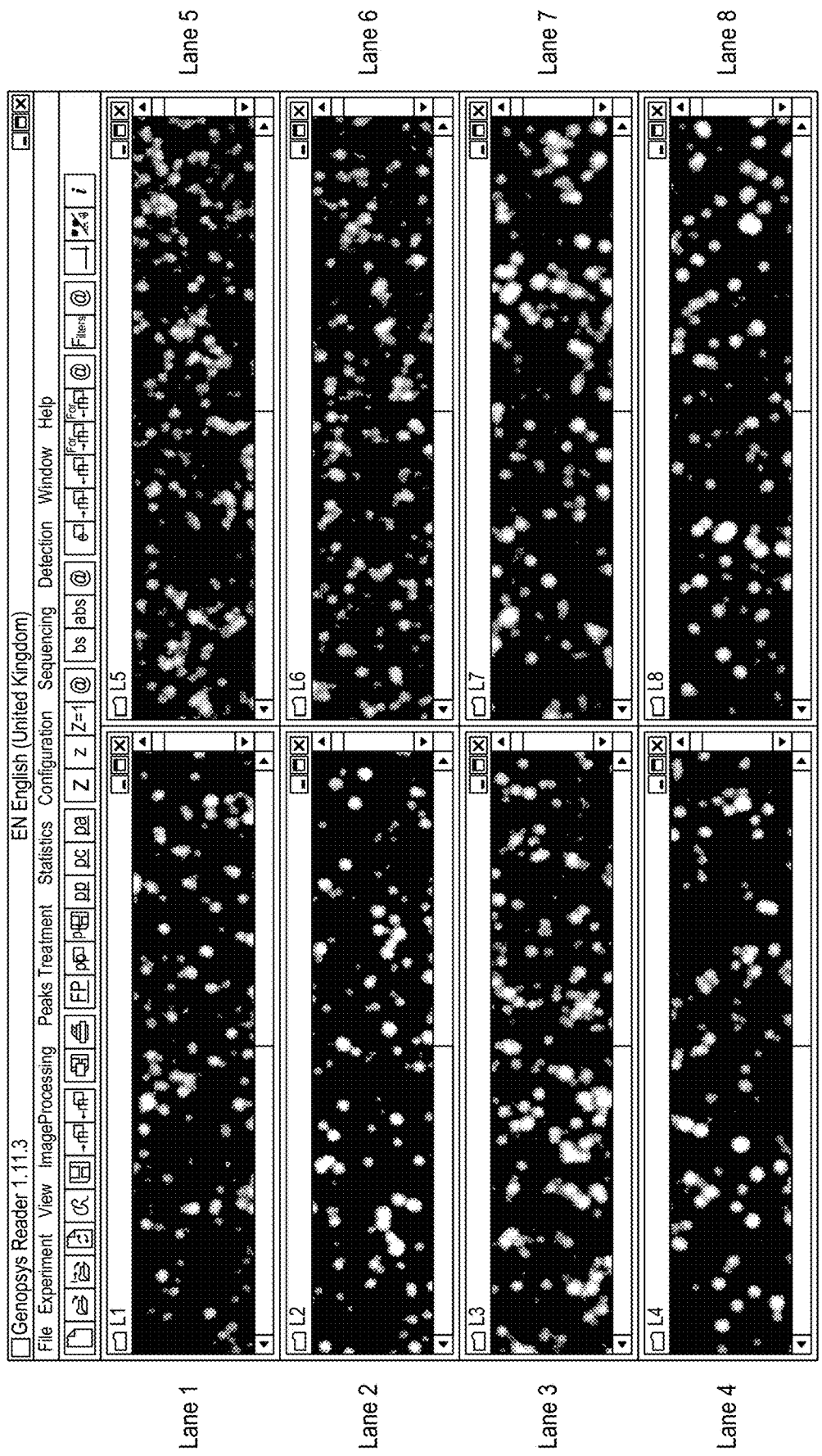
FIG. 4 shows tiles on a HiSeq Flow cell (Illumina Inc., San Diego, Calif.) stained with sybr green.

In a parallel experiment, clusters on a tile for each lane on a flow cell were visualized by staining with sybr green and imaged with a fluorescent microscope. FIG. 4 shows a tile for each lane on the flow cell stained with sybr green in which the reaction volume contained the following amounts of DNA: Lane 1: 300 ng E coli genomic DNA; Lane 2: 500 ng E coli genomic DNA; Lane 3: 300 ng human genomic DNA; Lane 4: 500 ng human genomic DNA; Lane 5: 300 ng Rhodobacter genomic DNA; Lane 6: 500 ng Rhodobacter genomic DNA; Lane 7: 300 ng Bacillus cereus genomic DNA; and Lane 8: 500 ng Bacillus cereus genomic DNA.

TABLE 4

| Lane | Tile | Clusters (raw) | Av 1st Cycle Intensity (PF) | % PF Clusters | % Align (PF) | % Error Rate (PF) | Read | Genome |
|---|---|---|---|---|---|---|---|---|
| 1 | 1115 | 356535 | 1302.32 | 93.65 | 91.03 | 0.12 | 1 | E coli |
| 1 | 1116 | 379029 | 1296.5 | 93.19 | 90.66 | 0.12 | 1 | E coli |
| 3 | 1215 | 214159 | 1261.95 | 84.69 | 77.68 | 0.46 | 1 | Human |
| 3 | 1216 | 189431 | 1313.34 | 85.83 | 76.94 | 0.43 | 1 | Human |
| 5 | 1215 | 394727 | 1218.33 | 89.61 | 91.16 | 0.39 | 1 | Rhodobacter |
| 5 | 1216 | 421620 | 1247.85 | 90.96 | 90.78 | 0.32 | 1 | Rhodobacter |
| 7 | 1215 | 198262 | 1316.33 | 85.26 | 80.55 | 0.31 | 1 | Bacillus cereus |
| 7 | 1216 | 221504 | 1324.36 | 87.24 | 80.11 | 0.24 | 1 | Bacillus cereus |

TABLE 5

| Lane | Tile | Clusters (raw) | Av 1st Cycle Intensity (PF) | % PF Clusters | % Align (PF) | % Error Rate (PF) | Read | Genome |
|---|---|---|---|---|---|---|---|---|
| 1 | 1215 | 374197 | 1247.61 | 93.47 | 88.87 | 0.18 | 2 | *E coli* |
| 1 | 1216 | 381833 | 1250.18 | 93 | 88.56 | 0.18 | 2 | *E coli* |
| 3 | 1215 | 214159 | 1136.26 | 84.69 | 75.96 | 0.45 | 2 | Human |
| 3 | 1216 | 189431 | 1142.97 | 85.83 | 75.42 | 0.46 | 2 | Human |
| 5 | 1215 | 394727 | 1138.29 | 89.61 | 86.33 | 0.77 | 2 | *Rhodobacter* |
| 5 | 1216 | 421620 | 1130.31 | 90.96 | 85.19 | 0.79 | 2 | *Rhodobacter* |
| 7 | 1215 | 198262 | 1183.26 | 85.26 | 78.98 | 0.33 | 2 | *Bacillus cereus* |
| 7 | 1216 | 221504 | 1154.88 | 87.24 | 78.2 | 0.29 | 2 | *Bacillus cereus* |

The term "comprising" as used herein is synonymous with "including," "containing," or "characterized by," and is inclusive or open-ended and does not exclude additional, unrecited elements or method steps.

As used herein, the term "each," when used in reference to a collection of items, is intended to identify an individual item in the collection but does not necessarily refer to every item in the collection. Exceptions can occur if explicit disclosure or context clearly dictates otherwise.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of preparing a population of target nucleic acids for sequencing comprising:
   (a) providing a substrate having a surface comprising capture probes;
   (b) contacting the surface with a reaction volume comprising a plurality of template nucleic acids and transposomes, wherein each transposome comprises a transposase and a transposon sequence comprising a sequence that hybridizes to the capture probes, wherein the template nucleic acids are prepared by contacting a target nucleic acid with the plurality of transposomes in the presence of the surface;
   (c) associating the template nucleic acids with the capture probes; and
   (d) sequencing the template nucleic acids on the surface.

2. The method of claim 1, comprising amplifying the associated template nucleic acids after (c) and before (d).

3. The method of claim 1, wherein the amplifying comprises bridge amplification on the surface.

4. The method of claim 1, wherein (a) comprises providing a sample comprising the target nucleic acid and the transposomes.

5. The method of claim 4, wherein the sample comprises a polymerase and/or a ligase.

6. The method of claim 1, wherein the capture probes comprise nucleic acids.

7. The method of claim 6, wherein (c) comprises hybridizing the template nucleic acids with the capture probes.

8. The method of claim 7, wherein (c) comprises preparing single-stranded template nucleic acids prior to hybridizing.

9. The method of claim 1, wherein either the plurality of template nucleic acids or the capture probes comprises an affinity moiety that is biotin and the other of the plurality of template nucleic acids and the capture probes comprises an affinity moiety that is avidin or streptavidin.

10. The method of claim 1, wherein the transposon sequence comprises a fragmentation site and the method comprises cleaving the fragmentation site.

11. The method of claim 10, wherein the fragmentation site is cleaved after (c).

12. The method of claim 1, wherein the transposase is removed from the template nucleic acids after (b) or after (c) by contacting the transposase with a protease or SDS.

13. The method of claim 1, wherein at least one transposome is different from at least one other transposome.

14. The method of claim 1, wherein sequencing on the surface comprises determining the proximity of sequences obtained from the template nucleic acids in a linear representation of the target nucleic acid sequence by determining the physical proximity of the captured template nucleic acids on the surface.

15. The method of claim 1, wherein the associated template nucleic acids are not amplified before the sequencing.

* * * * *

UNITED STATES PATENT AND TRADEMARK OFFICE
CERTIFICATE OF CORRECTION

| | | |
|---|---|---|
| PATENT NO. | : 11,299,765 B2 | |
| APPLICATION NO. | : 16/561483 | |
| DATED | : April 12, 2022 | |
| INVENTOR(S) | : Rigatti et al. | |

It is certified that error appears in the above-identified patent and that said Letters Patent is hereby corrected as shown below:

In the Claims

At Column 28, Line 19, in Claim 3, delete "claim 1" and insert --claim 2--.

Signed and Sealed this
Fifth Day of July, 2022

Katherine Kelly Vidal
*Director of the United States Patent and Trademark Office*